US007875612B2

(12) United States Patent
Green et al.

(10) Patent No.: US 7,875,612 B2
(45) Date of Patent: Jan. 25, 2011

(54) FOLATE MIMETICS AND FOLATE-RECEPTOR BINDING CONJUGATES THEREOF

(75) Inventors: Mark A. Green, West Lafayette, IN (US); Chun-Yen Ke, West Lafayette, IN (US); Christopher P. Leamon, West Lafayette, IN (US)

(73) Assignees: Purdue Research Foundation, West Lafayette, IN (US); Endocyte, Inc., West Lafayette, IN (US)

( * ) Notice: Subject to any disclaimer, the term of this patent is extended or adjusted under 35 U.S.C. 154(b) by 1656 days.

(21) Appl. No.: 10/475,876

(22) PCT Filed: Apr. 24, 2002

(86) PCT No.: PCT/US02/13045

§ 371 (c)(1),
(2), (4) Date: Jun. 21, 2004

(87) PCT Pub. No.: WO02/085908

PCT Pub. Date: Oct. 31, 2002

(65) Prior Publication Data

US 2004/0242582 A1 Dec. 2, 2004
US 2005/0227985 A9 Oct. 13, 2005

Related U.S. Application Data

(60) Provisional application No. 60/286,082, filed on Apr. 24, 2001.

(30) Foreign Application Priority Data

Apr. 24, 2002 (WO) ..................... PCT/US02/13045

(51) Int. Cl.
*A01N 43/64* (2006.01)
*A01N 43/58* (2006.01)
*A01N 43/60* (2006.01)
*A01N 43/90* (2006.01)
*A61K 31/53* (2006.01)
*A61K 31/50* (2006.01)
*A61K 31/495* (2006.01)
*A61K 31/519* (2006.01)
*C07D 253/08* (2006.01)
*C07D 487/00* (2006.01)
*C07D 475/00* (2006.01)

(52) U.S. Cl. ........................ 514/243; 514/248; 514/251; 514/262.1; 514/264.1; 544/183; 544/236; 544/256; 544/257; 544/280

(58) Field of Classification Search .................. 514/243
See application file for complete search history.

(56) References Cited

U.S. PATENT DOCUMENTS 2,515,483 A * 7/1950 Wolf et al. ................... 544/261

| | | |
|---|---|---|
| 2,816,110 A | 12/1957 | Sletzinger et al. |
| 3,387,001 A | 6/1968 | Hargrove et al. |
| 3,392,173 A | 7/1968 | Hargrove et al. |
| 4,166,810 A | 9/1979 | Cullinan et al. |
| 4,203,898 A | 5/1980 | Cullinan et al. |
| 4,337,339 A | 6/1982 | Farina et al. |
| 4,691,024 A | 9/1987 | Shirahata |
| 4,713,249 A | 12/1987 | Schroder |
| 4,801,688 A | 1/1989 | Laguzza et al. |
| 4,866,180 A | 9/1989 | Vyas et al. |
| 5,006,652 A | 4/1991 | Cullinan et al. |
| 5,094,849 A | 3/1992 | Cullinan et al. |
| 5,108,921 A | 4/1992 | Low et al. |
| 5,140,104 A | 8/1992 | Coughlin et al. |
| 5,266,333 A | 11/1993 | Cady |
| 5,416,016 A | 5/1995 | Low et al. |
| 5,417,982 A | 5/1995 | Modi |
| 5,547,668 A | 8/1996 | Kranz et al. |
| 5,552,545 A | 9/1996 | Pearce et al. |
| 5,635,382 A | 6/1997 | Low et al. |
| 5,672,486 A | 9/1997 | Soulillou |
| 5,688,488 A | 11/1997 | Low et al. |
| 5,998,603 A | 12/1999 | Cook |
| 6,004,555 A | 12/1999 | Thorpe et al. |
| 6,030,941 A | 2/2000 | Summerton et al. |
| 6,056,973 A | 5/2000 | Allen |
| 6,077,499 A | 6/2000 | Griffiths |
| 6,093,382 A | 7/2000 | Wedeking et al. |
| 6,171,614 B1 | 1/2001 | Chaikof et al. |

(Continued)

FOREIGN PATENT DOCUMENTS

CA   2372841   11/2000

(Continued)

OTHER PUBLICATIONS

Dorwald F. A. Side Reactions in Organic Synthesis, 2005, Wiley: VCH Weinheim p. IX of Preface.*

(Continued)

*Primary Examiner*—James O Wilson
*Assistant Examiner*—Jeffrey H Murray
(74) *Attorney, Agent, or Firm*—Barnes & Thornburg LLP

(57) ABSTRACT

A cell population expressing folate receptors is selectively targeted with a non-peptide folic acid analogue. The non-peptide folic acid analogue is conjugated to a diagnostic or therapeutic agent to enable selective delivery of the agent to the targeted cell population.

17 Claims, 8 Drawing Sheets

U.S. PATENT DOCUMENTS

| | | | |
|---|---|---|---|
| 6,171,859 | B1 | 1/2001 | Herrnstadt et al. |
| 6,177,404 | B1 | 1/2001 | DeFeo-Jones et al. |
| 6,184,042 | B1 | 2/2001 | Neumann et al. |
| 6,207,157 | B1 | 3/2001 | Gu et al. |
| 6,291,673 | B1 | 9/2001 | Fuchs et al. |
| 6,291,684 | B1 | 9/2001 | Borzilleri et al. |
| 6,335,434 | B1 | 1/2002 | Guzaev et al. |
| 6,365,179 | B1 | 4/2002 | Zalipsky et al. |
| 6,399,625 | B1 | 6/2002 | Zhu |
| 6,399,626 | B1 | 6/2002 | Zhu et al. |
| 6,399,638 | B1 | 6/2002 | Vite et al. |
| 6,432,973 | B1 | 8/2002 | Zhu et al. |
| 6,440,991 | B1 | 8/2002 | Zhu et al. |
| 6,511,986 | B2 | 1/2003 | Zhang et al. |
| 6,541,612 | B2 | 4/2003 | Molnar-Kimber et al. |
| 6,596,757 | B1 | 7/2003 | Chari et al. |
| 6,617,333 | B2 | 9/2003 | Raibindran et al. |
| 6,670,355 | B2 | 12/2003 | Azrulan et al. |
| 6,677,357 | B2 | 1/2004 | Zhu et al. |
| 6,680,330 | B2 | 1/2004 | Zhu et al. |
| 6,713,607 | B2 | 3/2004 | Caggiano et al. |
| 6,800,653 | B2 | 10/2004 | Regueiro-Ren et al. |
| 6,821,731 | B2 | 11/2004 | Gillis et al. |
| 6,915,855 | B2 | 7/2005 | Steele et al. |
| 6,958,153 | B1 | 10/2005 | Ormerod et al. |
| 7,019,014 | B2 | 3/2006 | Bernan et al. |
| 7,029,674 | B2 | 4/2006 | Carreno et al. |
| 7,033,594 | B2 | 4/2006 | Low et al. |
| 7,060,709 | B2 | 6/2006 | Cooperstone et al. |
| 7,060,797 | B2 | 6/2006 | O'Toole et al. |
| 7,067,111 | B1 | 6/2006 | Yang et al. |
| 7,074,804 | B2 | 7/2006 | Zhu et al. |
| 7,105,328 | B2 | 9/2006 | Wood et al. |
| 7,122,361 | B2 | 10/2006 | Liu et al. |
| 7,128,893 | B2 | 10/2006 | Leamon et al. |
| 7,153,957 | B2 | 12/2006 | Chew et al. |
| 7,601,332 | B2 | 9/2009 | Vlahov et al. |
| 2003/0086900 | A1 | 5/2003 | Low et al. |
| 2003/0162234 | A1 | 8/2003 | Jallad |
| 2004/0018203 | A1 | 1/2004 | Pastan et al. |
| 2004/0033195 | A1 | 2/2004 | Leamon et al. |
| 2004/0242582 | A1 | 12/2004 | Green et al. |
| 2005/0004010 | A1 | 1/2005 | Collins et al. |
| 2005/0026068 | A1 | 2/2005 | Gogolides et al. |
| 2005/0107325 | A1 | 5/2005 | Manoharan et al. |
| 2005/0165227 | A1 | 7/2005 | Vlahov et al. |
| 2005/0227985 | A9 | 10/2005 | Green et al. |
| 2005/0239713 | A1 | 10/2005 | Domling et al. |
| 2005/0239739 | A1 | 10/2005 | Matulic-Adamic et al. |
| 2006/0058266 | A1 | 3/2006 | Manoharan et al. |
| 2006/0128754 | A1 | 6/2006 | Hoefle et al. |
| 2007/0009434 | A1 | 1/2007 | Low et al. |
| 2007/0275904 | A1 | 11/2007 | Vite et al. |
| 2008/0207625 | A1 | 8/2008 | Xu et al. |
| 2008/0248052 | A1 | 10/2008 | Vlahov et al. |
| 2008/0280937 | A1 | 11/2008 | Leamon et al. |
| 2009/0203889 | A1 | 8/2009 | Vlahov et al. |
| 2010/0004276 | A1 | 1/2010 | Vlahov et al. |
| 2010/0048490 | A1 | 3/2010 | Vlahov et al. |
| 2010/0104626 | A1 | 4/2010 | Leamon et al. |

FOREIGN PATENT DOCUMENTS

| | | |
|---|---|---|
| CA | 2376175 | 12/2000 |
| EP | 0 116 208 A1 | 8/1984 |
| EP | 0 163 550 A2 | 12/1985 |
| EP | 0 247 792 | 12/1987 |
| EP | 0116208 | 3/1988 |
| EP | 0 280 741 A1 | 9/1988 |
| EP | 0 354 728 | 2/1990 |
| JP | 59-175493 | 10/1984 |
| JP | 60-255789 | 12/1985 |
| WO | WO 88/01622 | 3/1988 |
| WO | WO 90/12096 | 10/1990 |
| WO | WO 91/07418 | 5/1991 |
| WO | WO96/36367 | 11/1996 |
| WO | WO 98/10651 A1 | 3/1998 |
| WO | WO 99/20626 A1 | 4/1999 |
| WO | WO 99/61055 | 12/1999 |
| WO | WO 00/35422 | 6/2000 |
| WO | WO 00/66091 | 11/2000 |
| WO | WO 00/74721 | 12/2000 |
| WO | WO 01/28592 | 4/2001 |
| WO | WO 01/74382 | 10/2001 |
| WO | WO 02/085908 A1 | 10/2002 |
| WO | WO 02/087424 | 11/2002 |
| WO | WO 02/098868 | 12/2002 |
| WO | WO 03/097647 | 11/2003 |
| WO | WO 2004/005326 | 1/2004 |
| WO | WO 2004/005327 | 1/2004 |
| WO | WO 2004/012735 | 2/2004 |
| WO | WO 2004/046170 | 6/2004 |
| WO | WO 2004/054622 | 7/2004 |
| WO | WO 2004/069159 | 8/2004 |
| WO | WO2004/100983 | 11/2004 |
| WO | WO 2005/074901 | 8/2005 |
| WO | WO 2005/112919 | 12/2005 |
| WO | WO 2006/012527 | 2/2006 |
| WO | WO 2006/042146 | 4/2006 |
| WO | WO 2006/101845 | 9/2006 |
| WO | WO2006/105141 | 10/2006 |
| WO | WO 2007/022493 | 2/2007 |
| WO | WO 2007/022494 | 2/2007 |
| WO | WO 2008/101231 | 8/2008 |
| WO | WO 2008/112873 | 9/2008 |
| WO | WO 2009/002993 | 12/2008 |
| WO | WO 2009/055562 | 4/2009 |

OTHER PUBLICATIONS

Weygand, et. al., Chemische Berichte (1950), 83, 460-67.*

Nimmo-Smith, et. al., Journal of General Microbiology (1953), 9, 536-44.*

Garrett et al. "Synthesis and characterisation of polyamine-poly(ethylene glycol) constructs for DNA binding and gene delivery" *Bioorganic & Medicinal Chemistry*, 2000; 8: 1779-1797.

Huang et al. "Design, synthesis and sequence selective DNA cleavage of functional models of bleomycin-II. 1,2-trans-disubstituted cyclopropane units as novel linkers" *Bioorganic and Medicinal Chemistry*, vol. 3, No. 6, Jun. 1995, pp. 647-657.

Lee et al. "Prolonged circulating lives of single-chain Fv proteins conjugated with polyethylene glycol: a comparison of conjugation chemistries and compounds" *Bioconjugate Chem*. 1999;10:973-81.

Mehvar R. "Dextrans for targeted and sustained delivery of therapeutic and imaging agents" *Journal of Controlled Release*, 2000; vol. 69, No. 1, pp. 1-25.

Peterson et al. "Enzymatic cleavage of peptide-linked radiolabels from immunoconjugates" *Bioconjug. Chem*., 1999; 10: 553-557.

Tanaka et al., "Preparation and Characterization of a Disulfide-linked Bioconjugate of Annexin V with the B-chain of Urokinase: An Improved Fibrinolytic Agent Targeted to Phospholipid-containing Thrombi," *Biochem.*, 1996; vol. 35, No. 3, pp. 922-929.

Thaden et al., "Photoaffinity behavior of a conjugate of oligonucleoside methylphosphonate, rhodamine, and psoralen in the presence of complementary oligonucleotides." *Bioconjugate Chem*. 1993; 4: 386-394.

Crapatureanu et al., "Molecular Necklaces. Cross-linking Hemoglobin with Reagents Containing Covalently Attached Ligands" *Bioconjugate Chemistry*, 1999 10(6), 1058-1067.

Leamon Christopher P., "Aspects of Folate-Mediated Drug Delivery . . . Beyond Purdue" PowerPoint Presentation presented at Purdue University on May 4, 1999, (22 pages).

Achilefu et al. "A New Method for the Synthesis of Tri-*tert*-butyl Diethylenetriaminepentaacetic Acid Its Derivatives" *J. Org. Chem.* 2000;65:1562-1565.

Anderson et al. "Potocytosis: Sequestration and transport of small molecules by caveolae" *Science* 1992;255(5043):410-411.

Antony et al. "Studies of the role of a particulate folate-binding protein in the uptake of 5-methyltetrahydrofolate by cultured human KB cells" *J. Biol. Chem.* 1985;260(28):14911-14917.

Campbell et al., "Folate-Binding Protein is a Marker for Ovarian Cancer" *Cancer Res.*, 1991;51(19):5329-5338.

Carl et al. "A novel connector linkage applicable in prodrug design" *J. Med Chem.* 1981;24(5):479-480.

Coney et al. "Cloning of a tumor-associated antigent: MOv18 and MOv19 antibodies recognize a folate-binding protein" *Cancer Res.* 1991;51(22):6125-32.

Crapatureanu et al. "Molecular necklaces. Cross-linking hemoglobin with reagents containing covalently attached ligands" *Bioconjugate Chemistry*, 1999;10(6):1058-67. Abstract Only.

Darnell, Ed. *Molecular Cell Biology* W. H. Freeman, San Francisco 1990;326-333.

DeNardo, Gerald. "When is Too Much Too Much and Yet Not Enough? Alas, a Plethora of Opportunities but Where's the Beef?" *J. of Nuclear Medicine* 2000;41(3):470-3.

Forgac. "Structure and function of vacuolar class of ATP-driven pumps" *Physiological Rev.* 1989;69(3):765-795.

Garin-Chesa et al. "Trophoblast and ovarian cancer antigen LK26: Senstivity and specificity in immunopathology and molecular identification as a folate-binding protein" *Am. J. Pathol.* 1993;142(2):557-567.

Garrett et al. "Synthesis and characterisation of polyamine-poly(ethylene glycol) constructs for DNA binding and gene delivery" *Bioorganic & Medicinal Chemistry*, 2000;8(7):1779-1797. Abstract Only.

Henderson et al. "Mediated uptake of folate by a high-affinity binding protein in sublines of L1210 cells adapted to nanomolar concentrations of folate" *J. Membrane Biol.*, 1988;101:247-258.

Huang et al. "Design, syntheses and sequence selective DNA cleavage of functional models of bleomycin-II. 1,2-trans-disubstituted cyclopropane units as novel linkers" *Bioorganic & Medicinal Chemistry*, 1995;3(6):647-57. Abstract Only.

Jansen et al., "Identification of a Membrane-Associated Folate-Binding Protein in Human Leukemic CCRF-CEM Cells with Transport-Related Methotrexate Resistance"in *Cancer Res.*, 1989, 49, 2455-2459.

Jansen, "Receptor- and Carrier-Mediated Transport Systems for Folates and Antifolates," *Antifolate Drugs in Cancer Therapy*, Jackman, Ed., Humana Press Inc, Totowa NJ (1999): 293-321.

Jansen et al. "The Reduced Folate/Methotrexate Carrier and a Membrane-Associated Folate Binding Protein as Transport Routes for Novel Antifolates: Structure-Activity Relationship" *Chemistry and Biology of Pteridines and Folates* New York, 1992;767-770.

Kamen et al.,"Delivery of folates to the cytoplasm of MA104 Cells in Mediated by a Surface Membrane Receptor that Recycles" *J. Biol. Chem.* 1988;263(27):13602-13609.

Kamen et al., 1986, "Receptor-mediated folate accumulation is regulated by cellular folate content" *Proc. Natl. Acad. Sci.*, U.S.A. 83, 5983-5987.

Ke et al. "Targeting the Tumor-Associated Folate Receptor with a $^{111}$IN-DTPA Conjugate of Pteroic Acid" Abstract No. 427. 48th Annual Meeting of the Society of Nuclear Medicine Toronto, Canada, Jun. 26, 2001, available May 4, 2001; 1 pg.

Kemp et al. "New Protective Groups for Peptide Synthesis—I The Bic Group Base and Solvent Lability of the 5-Benzisoxazolymethyleneoxycarbonylamino function" *Tet. Lett.* 1975;52:4625-4628.

Kumar et al., "Folate Transport in *Lactobacillus salivarius*" *J. Biol. Chem.* 1987;262(15):7171-9.

Kutsky RJ. *Handbook of Vitamins, Minerals, and Hormones*, 2nd Edition. New York: Van Nostrand Reinhold: 1981;263-277.

Leamon et al. "Delivery of macromolecules into living cells: A method that exploits folate receptor endocytosis" *Proc Natl Acad Sci*, 1991, 88:5572-5576.

Leamon et al., "Cytotoxicity of Momordin-folate Conjugates in Cultured Human Cells" *J. Biol. Chem.*, 1992;267:24966-24971.

Leamon et al. "Membrane folate-binding proteins are responsible for the folate-protein conjugate endocytosis into cultured cells" *Biochem. J.* 1993;291:855-860.

Leamon et al., "Cytotoxicity of Folate-pseudomonas Exotoxin Conjugates Towards Tumor Cells" *J. Biol. Chem.*, 1993;268:24847-24854.

Leamon et al. "Selective targeting of malignant cells with cytotoxin-folate conjugates" *J. Drug Targeting* 1994;2(2):101-112.

Leamon et al., "Folate-mediated drug delivery: effect of alternative conjugative chemistry" *J. Drug Targeting* 1999;7(3):157-169.

Lee et al., "Delivery of Liposomes into Cultured KB Cells via Folate Receptor-mediated Endocytosis" *J. Biol. Chem.*, 1994;269(5):3198-3204.

Lee et al. "Folate-mediated tumor cell targeting of liposome-entrapped doxorubicin in vitro" *Biochim. Biophys. Acta*, 1995;1233(2):134-144.

Lee et al. "Prolonged circulating lives of single-chain Fv proteins conjugated with polyethylene glycol: a comparison of conjugation chemistries and compounds" *Bioconjugate Chemistry*, 1999;10(6):973-81. Abstract Only.

Li et al. "Local concentration of folate binding protein GP38 in sections of human ovarian carcinoma by concentration of in vitro quantitative autoradiography." *J. Nucl. Med.* 1996;37:665-672.

Linder et al., In vitro & in vivo studies with α-and γ-isomers of $^{99m}$Tc-oxa folate show uptake of both isomers in folate receipt (+) KB Cell Lines *J. Nuclear Med.* 2000;41(5):470 Suppl.

Luo et al., "Efficient Syntheses of Pyrofolic Acid and Pteroyl Azide, Reagents for the Production of Carboxyl-Differentiated Derivatives of Folic Acid" *J. Am. Chem. Soc.* 1997;119:10004-10013.

Mathias et al. "Indium [111In] DTPA-Folate as a potential Folate-Receptor-Targeted Radiopharmaceutical" *J. Nucl. Med.* 1998;39:1579-1585.

Mathias et al. "Receptor-Mediated Targeting of $^{67}$Ga-Deferoxamine-Folate-Receptor-Targeted Radiopharmaceutical" *Nucl. Med. Biol.* 1999;26(1):23-5.

Mathias et al. Synthesis of [$^{99m}$Tc] DTPA-Folate and Its Evaluation as a Folate-Receptor-Targeted Radiopharmaceutical, *Bioconjugate Chemistry* 2000;11:253-257.

Mathias et al. "Tumor-selective radiopharmaceutical targeting via receptor-mediated endocytosis: evaluation of a gallium-67 labeled deferoxamine-folate." *J. Nucl. Med.* 1996;37(6):1003-1008.

McAlinden et al., "Synthesis and biological evaluation of a fluorescent analogue of folic acid" *Biochemistry* 1991;30(23):5674-5681.

Mehvar R "Dextrans for targeted and sustained delivery of therapeutic and imaging agents" [Review] *Journal of Controlled Release*, 2000;69(1):1-25. Abstract Only.

Mezzanzanica et al. "Human T-lymphocytes targeted against an established human ovarian carcinoma with a bispecific F(ab')2 antibody prolong host survival in a murine xenograft model" *Cancer Res.* 1991;51:5716-5721.

Miotti et al., "Characterization of Human Ovarian Carcinoma-Associated Antigens Defined by Novel Monoclonal Antibodies with Tumor -Restricted Specificity" *Int. J. Cancer*, 1987;39:297-303.

Nomura et al."Development of an efficient intermediate, α-[2-(trimethylsilyl)ethoxy]-2-N-[2-(trimethylsilyl)ethoxycarbonyl]folic acid, for the synthesis of folate (γ)-conjugates, and its application to the synthesis of folate-nucleoside conjugates." *J. Org. Chem.* 2000;65(16):5016-5021.

Pastan et al, eds. "The Pathways of Endocytosis" *Endocytosis*, Plenum Press, New York 1985;1-40.

Peterson et al. "Enzymatic cleavage of peptide-linked radiolabels from immunoconjugates" *Bioconjugate Chemistry*, 1999;10(4):553-7. Abstract Only.

Pizzorno et al. "5,10-Dideazatetrahydrofolic acid (DDATHF) transport in CCRF-CEM and MA104 cell lines." *J. Biol, Chem.*, 1993;268(2):247-258.

Rothenberg et al. "Further observations on the folate-binding factor in some leukemic cells" *J. Clin. Invest.* 1971;50(3):719-726.

Selhub et al. "The folate binding protein of rat kidney. Purification, properties, and cellular distribution" *J. Biol. Chem.* 1984;259(10):6601-6606.

Selhub et al. "Renal folate adsorption and the kidney folate binding protein I. Urinary Clearance studies" *Am. J. Physiol.* 252:F750-F756.

Selhub et al. "Renal folate adsorption and the kidney folate binding protein II. Microinfusion studies" *Am. J. Physiol.* 252:F757-F760.

Senter et al. "Development of a Drug-Release Strategy Based on the Reductive Fragmentation of Benzyl Carbamate Disulfides" *J. Org. Chem.* 1990;55:2975-2978.

Sirotnak. "Obligate genetic expression in tumor cells of a fetal membrane property mediating "Folate" transport: biological significance and implications for improved therapy of human cancer" *Cancer Res.*, 1985;45(9):3992-4000.

Stein et al. "Normal tissue reactivity of four anti-tumor monoclonal antibodies of clinical interest" *Int. J. Cancer* 1991;47(2):163-169.

Tanaka et al. "Preparation and characterization of a disulfide-linked bioconjugate of annexin V with the B-chain of urokinase: an improved fibrinolytic agent targeted to phospholipid-containing thrombi" *Biochemistry*, 1996;35(3):922-9. Abstract Only.

Thaden et al. "Photoaffinity behavior of a conjugate of oligonucleoside methylphosphonate, rhodamine, and psoralen in the presence of complementary oligonucleotides" *Bioconjugate Chemistry*, 1993;4(5):386-94. Abstract Only.

Toffoli et al. "Expression of folate binding protein as a prognostic factor for response to platinum-containing chemotherapy and survival in human ovarian cancer" *Int. J. Cancer (Pred. Oncol.)* 1998;79:121-126.

Toffoli et al. "Overexpression of folate binding protein in ovarian cancers" *Int J. Cancer (Pred. Oncol.)* 1997;74:193-198.

Turek et al. "Endocytosis of folate-protein conjugates: Ultrastructural localization in KB cells" *J. Cell Sci.*, 1993;106:423-430.

Wang et al., "Delivery of Antisense Oligodeoxyribonucleotides Against the Human Epidermal Growth Factor Receptor into Cultured Kb Cells with Liposomes Conjugated to Folate via Polyethyleneglycol" in *Proc. Natl. Acad. Sci.* U.S.A., 1995, 92, 3318-3322.

Wang et al. "Design and Synthesis of [$^{111}$In] DTPA-Folate for Use as a Tumor-Targeted Radiopharmaceutical" *Bioconj. Chem.* 1997;8(5):673-679.

Wang et al., "Synthesis, Purification and Tumor Cell Uptake of $^{67}$Ga-deferoxamine-folate, a Potential Radiopharmaceutical for Tumor Imaging" *Bioconj. Chem.*, 1996;7, 56-62.

Weitman et al. "Distribution of the folate receptor GP38 in normal and malignant cell lines and tissues" *Cancer Res.* 1992;52(12):3396-3401.

Westerhof et al. "Membrane transport of natural folates and antifolate compounds in murine L1210 Leukemia cells: role of carrier-and receptor-mediated transport systems" *Cancer Res.* 1991;51:5507-5513.

Westerhof et al. "Carrier- and receptor-mediated transport of folate antagonists targeting folate-dependent enzymes: correlates of molecular-structure and biological activity" *Mol. Pharm.*, 1995, 48(3):459-471.

Williams et al. "Renal tubular transport of folic acid and methotrexate in the monkey" *Am. J. Physiol* 1982;242(5):F484-490.

Wu et al., "Clustering of GPI-anchored folate receptor independent of both cross-linking and association with caveolin" *J. Membrane Biol.* 1997;159(2):137-147.

Agoston E.S. et al., "Vitamin D Analogs as Anti-Carcinogenic Agents," *Anti-Cancer Agents in Medicinal Chemistry.* 2006: 6(1): 53-71.

U.S. Appl. No. 12/775,824, filed May 7, 2010, Green et al.

Agoston E.S. et al., "Vitamin D Analogs as Anti-Carcinogenic Agents," *Anti-Cancer Agents in Medicinal Chemistry.* 2006: 6(1): 53-71.

Antony A.C., "Folate receptors," *Annu Rev Nutr*, 1996; 16: 501-21.

Antony A.C., "The biological chemistry of folate receptors," *Blood*, 1992; 79(11):2807-2820.

Archer M.C. et al., "Separation of Folic Acid Derivatives and Pterins by High-Performance Liquid Chromatography." *Methods In Enzymology.* 1980: 66: pp. 452-459.

Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.

Ayers W.A., "Effect of Vitamin B12 and Analogs on the Respiration of a Marine Bacterium," *Archives of Biochemistry and Biophysics*, 1962, vol. 96, pp. 210-215.

Barnett C.J. et al., "Structure-Activity Relationships of Dimeric Catharanthus Alkaloids. 1. Deacetylvinblastine Amide (Vindesine) Sulfate," *J. Med. Chem.* 21: 88-96 (1978).

Bavetsias, V. et al., "Design and synthesis of Cyclopenta[g]quinazoline-based antifolates as inhibitors of thymidylate synthase and potential antitumor agents." J Med Chem. 2000: 43(10): 1910-1926.

Bavetsias, V., et al., "The design and synthesis of water-soluble analogues of CB30865, a quinazolin-4-one-based antitumor agent " J Med Chem. 2002. 45(17): 3692-3702.

Birinberg E. M. et al., "Synthesis and antimetabolic activity of pyrimidine analogs of folic and pteroic acids." *Pharmaceutical Chemistry Journal.* 1969: 3(6): pp. 331-333.

Bock et al., "Sulfonamide structure-activity relationships in a cell-free system. 2. Proof for the formation of a sulfonamide-containing folate analog," *Journal of Medical Chemistry*, 17: 23-28 (1974).

Boger, D.L. et al., "An improved synthesis of 1,2,9,9a-tetrahydrocyclopropa[c]benz[e]indol-4-one (CBI): a simplified analog of the CC-1065 alkylation subunit." *J. Ore. Chem.*, 1992: 57: 2873-2876.

Cho et al., "Single-chain Fv/folate conjugates mediate efficient lysis of folate-receptor-positive tumor cells," *Bioconjug. Chem.* 8(3): 338-346 (1997).

Christensen et al., "Membrane receptors for endocytosis in the renal proximal tubule," *Int. Rev. Cytol.*, 1998; 180: 237-284.

Churlaud C. et al., "Novel 4-(Trimethylsilyl)aminoalkanes and 4-(Trimethylsilyl)aminoalk-2-enes, via a 1,5-Hydride Shift, in the Reaction of α-Unsaturated Silanes with Aminomethylbenzotriazoles," *Organomettalics*, 1999; 18(21): 4270-4274.

Citro G. et al., "Inhibition of leukemia cell proliferation by folic acid - polylysine-mediated introduction of c-myb antisense oligodeoxynucelotides into HL-60 cells," *Br. J. Cancer*, 1994; 69: 463-467.

Cope A.C. et al., "Thermal Rearrangement of Allyl-type Sulfoxides, Sulfones and Sulfinates," *J. Am. Chem. Soc.*, 1950: 72: 59-67.

Cosulich D.B. et al., "Analogs of Pteroylglutamic Acid. 1. N10-Alkylpteroic Acid and Derivatives," *JACS.* 1948. 70 (5). pp. 1922-1926.

DeVita, Jr., Vincent et al (eds); *Biologic Therapy of Cancer*; 2nd ed., J.B. Lippincott Company; 1995.

Domling A. et al., "Myxobacterial Epothilones and Tubulysins as Promising Anticancer Agents," *Molecular Diversity.* 2005: 9: 141-147.

Douglas J.T. et al., "Targeted Gene Delivery by Tropism-Modified Adenoviral Vectors," *Nat. Biotechnol.*, 1996, vol. 14, pp. 1574-1578.

Eichman, J.D. et al., "The Use of PAMAM Dendrimers In The Efficient Transfer Of Genetic Material Into Cells", Jul. 2000, *PSIT*, vol. 3, No. 7, pp. 232-245.

Foong, L.Y. et al., "Development of a Novel Thiol Reagent for Probing Ion Channel Structure: Studies in a Model System," Biochemistry, 1997, vol. 36, pp. 1343-1348.

Frankel AA., "Immunotoxin therapy of cancer," *Oncology*, 1993; 7(5): 69-78.

Shealy Y.F., "Synthesis and Evaluation of Some New Retinoids for Cancer Chemoprevention," *Preventive Medicine*, 1989, vol. 18, pp. 624-645.

Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," *J Med Chem.*, 2008; 51(15):4589-4600.

Gibbs, DD et al., "BGC 945, a novel tumor-selective thymidylate synthase inhibitor targeted to alpha-folate receptor-overexpressing tumors," Cancer Res, 2005; 65(24): 11721-11728.

Gottschalk S. et al., "Folate receptor mediated DNA delivery into tumor cells: potosomal disruption results in enhanced gene expression," *Gene Therapy*, 1994; 1(3): 185-191.

Greene T.E. et al., "Protective Groups ion Organic Synthesis," 2d edition, John Wiley & Sons, Inc. New York (1991).

Hanck A.B. et al., "Dexpanthenol (Ro 01-4709) in the treatment of constipation," *Acta Vitaminol Enzymol*, 1982; vol. 4 (1-2), pp. 87-97 (abstract only).

Harvison, P.J. et al., "Synthesis and Biological Activity of Novel Folic Acid Analogues: Pteroyl-S-alkylhomocysteine Sulfoximines," *Journal of Medicinal Chemistry*, 1992, vol. 35, pp. 1227-1233.

U.S. Appl. No. 60/946,092, filed Jun. 25, 2007, Vlahov et al.
U.S. Appl. No. 60/982,595, filed Nov. 25, 2007, Vlahov et al.
U.S. Appl. No. 61/036,176, filed Mar. 13, 2008, Vlahov et al.
U.S. Appl. No. 61/036,186, filed Mar. 13, 2008, Vlahov et al.
U.S. Appl. No. 12/739,579, filed Apr. 23, 2010, Vlahov et al.
U.S. Appl. No. 12/775,824, filed May 7, 2010, Green et al.

Henderson, E.A. et al., Targeting the alpha-folate receptor with cyclopenta[g]quinazoline-based inhibitors of thymidylate synthase. Bioorg Med Chem. 2006. 14(14): 5020-5042.

Ho R. I. et al., "A simple radioassay for dihydrofolate synthetase activity in *Escherichia coli* and its application to an inhibition study of new pteroate analogs," *Anal. Biochem.*, 1976, 73(2), pp. 493-500.

Hofland et al., "Folate-targeted gene transfer in vivo," *Mol Ther* 5(6): 739-744 (2002).

Hofle, G. et al., "Semisynthesis and Degradation of the Tubulin Inhibitors Epothilone and Tubulvsin". 2003. *Pure Annl. Chem..* vol. 75. Nos. 2-3. pp. 167-178.

Holladay et al., "Riboflavin-mediated delivery of a macromolecule into cultured human cells," *Biochim Biophys Acta*, 1426(1): 195-204 (1999).

Holm, J. et al., "Folate receptors in malignant and benign tissues of human female genital tract," *BioSci. Rep.*, 17(4): 415-427 (1997).

Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).

Hosomi A. et al., "Affinity for a-tocopherol transfer protein as a determinant of the biological activities of vitamen E analogs," *Federation of European Biochemical Societies Letters*, 1997, vol. 409, pp. 105-108.

Houlihan, C. M. et al., "Preparation and Purification of Pteroic Acid from Folic Acid," *Analytical Biochemistry*. 1972. vol. 46, pp. 1-6.

Hynes et al., "Quinazolines as inhibitors of dihydrofolate reductase. 4. Classical analogues of folic and isofolic acids". *Journal of Medical Chemistry*. 1977: 20: 588-591.

Jackman, A. L. et al., "Antifolates targeted specifically to the folate receptor," Adv Drug Deliv Rev, 2004; 56(8): 1111-1125.

Jones T.R. et al., "A potent antitumour quinazoline inhibitor of thymidylate synthetase: synthesis, biological properties and therapeutic results in mice." *Eur J Cancer*, 1981: 17(11:11-9.

Jones T.R. et al., "Quinazoline antifolates inhibiting thymidylate synthase: variation of the amino acid," *J Med Chem*, 1986; 29(6):1114-8.

Jung K.H. et al., "Intramolecular o-glycoside bond formation," *Chem. Rev.*, 2000, 100, 4423-42.

Kagechika H et al., "Synthetic Retinoids: Recent Developments Concerning Structure and Clinical Utility," *Journal of Medicinal Chemistry*, 2005; vol. 48, No. 19, pp. 5875-5883.

Kamen et al., "The folate receptor works in tandem with a probenecid-sensitive carrier in MA104 cells in vitro." *J. Clin. Invest.*, 87(4): 1442-1449 (1991).

Kamen, B. A. et al., "Receptor-mediated folate accumulation is regulated by the cellular folate content " *Proc. Natl. Acad. Sci. USA.* 83: 5983-5987 (1986).

Kandiko C.T. et al., "Inhibition of Rat Brain Pyruvate Dehydrogenase by Thiamine Analogs," *Biochemical Pharmacology*. 1988: vol. 37. No. 22. pp/ 4375-4380.

Kane et al., "The influence of extracellular folate concentration on methotrexate uptake by human KB cells. Partial characterization of a membrane-associated methotrexate binding protein," *J. Biol. Chem.*, 261: 44-49 (1986).

Kim et al., "Synthesis and biological activity of 10-thia-10-deaza analogs of folic acid, pteroic acid, and related compounds". *Journal of Medical Chemistry*, 18: 776-780 (1975).

Kranz et al., "Conjugates of folate and anti-T-cell-receptor antibodies specifically target folate-receptor-positive tumor cells for lysis," *Proc. Natl. Acad. Sci. USA*, 1995; 92(20), pp. 9057-9061.

Ladino et al., "Folate-maytansinoids: target-selective drugs of low molecular weight," *Int. J. Cancer*, 73(6): 859 864 (1997).

Lambooy J. P., "Riboflavin Analogs Utilized for Metabolism by a Lactobacillus Casei Mutant," *Int. J. Biochem.*, vol. 16, No. 2, 1984, pp. 231-234.

Landuer W. et al., "The Interaction in Teratogenic Activity of the Two Niacin Analogs 3-acetylnyridine and 6-aminonicotinamide." *J Exp Zool*, 151(3):253-258 (1962).

Langone, J.J., et al., "Radioimmunoassays For The Vinca Alkaloids, Vinblastine And Vincristine" 1979 *Analytical Biochemistry* No. 95, pp. 214-221.

Larock R.C., "Comprehensive Organic Transformations, a guide to functional group preparations," VCH Publishers. Inc. New York (1989).

Leamon CP et al., "Comparative Preclinical Activity of the Folate-targeted Vinca Alkaloid Conjugates EC140 and EC145," *Int J Cancer*, 2007; 121(7):1585-92.

Leamon CP et al., "Folate-mediated targeting: from diagnostics to drug and gene delivery," *Drug Discovery Today* 6: 36-43 (2001).

Leamon CP et al., "Folate-targeted chemotherapy," *Adv Drug Deliv Rev*, 2004;56(8): 1127-41.

Leamon CP et al., "Synthesis and biological evaluation of EC140: A novel folate-targeted vinca alkaloid conjugate," *Bioconjug Chem*, 2006;17(5):1226-32.

Leamon CP et al., "Synthesis and Biological Evaluation of EC20: A New Folate-Derived, (99m)Tc-Based Radiopharmaceutical," *Bioconjug. Chem*. 13(6): 1200-1210 (2002).

Leamon CP et al., "Synthesis and biological evaluation of EC72: a new folate-targeted chemotherapeutic," *Bioconjug Chem.*, 2005:16(4):803-11.

Lee et al, "Measurement of Endosome pH Following Folate Receptor-Mediated Endocytosis," *Biochim, Biophys. Acta* 1312(3): 237-242 (1996).

Lee W.W. et al., "Folic acid antagonists. Methotrexate analogs containing spurious amino acids. Dichlorohomofolic acid." *Journal of Medical Chemistry*. 17: 326-330 (1974).

Lee et al., "Synthesis and evaluation of taxol-folic acid conjugates as targeted antineoplastics," *Bioorg Med Chem*. 10(7): 2397-2414, (2002).

Lee, Francis Y. F., et al., "BMS-247550: A Novel Epothilone Analog With A Mode Of Action Similar To Paclitaxel But Possessing Superior Antitumor Efficacy," *Clin Cancer Res*. 2001, No. 7, pp. 1429-1437.

Lee, R. J. and Huang, L., "Folate-Targeted, Anionic Liposome-Entrapped Polylysine-Condensed Dna For Tumor Cell-Specific Gene Transfer," *J. Biol. Chem*. 271(14): 8481-8487 (1996).

Lemon, Julia, et al., "Conversion of Pterolyglutamic Acid To Pteroic Acid By Bacterial Degradation," *Archives of Biochemistry*, 1948; vol. 19, pp. 311-316.

Levy, Carl C., et al. "The Enzymatic Hydrolysis Of Methotrexate And Folic Acid", 1967, *The Journal Of Biological Chemistry*, vol. 242, No. 12, pp. 2933-2938.

Lewis et al., "Receptor-mediated folate uptake is positively regulated by disruption of actin cytoskeleton." Cancer Res 58(14): 2952-2956 (1998).

Li et al, "Targeted delivery of antisense oligodeoxynucleotides by LPDII," *J. Liposome Res*. 7(1): 63 (1997).

Liu et al., "Targeted Drug Delivery to Chemoresistant Cells: Folic Acid Derivatization of FdUMP[10] Enhances Cytotoxicity Toward 5-Fu-Resistant Human Colorectal Tumor Cells," *J. Org. Chem*. 66: 5655-5663 (2001).

Lonsdale D, "A Review of the Biochemistry, Metabolism and Clinical Benefits of Thiamin(e) and Its Derivatives," publication, Advance Access Publication, vol. 3, Feb. 2006, pp. 49-59.

Lopes et al., "Acyloxymethyl as a drug protecting group. Part 5.1 Kinetics and mechanism of the hydrolysis of tertiary N-acyloxymethylsulfonamides," *J. Chem. Soc.*, Perkin Trans. 2, pp. 431-439 (1999).

Low P.S. et al., "Folate Receptor-Targeted Drugs for Cancer and Inflammatory Diseases," *Adv Drug Deliv Rev*, 2004;56(8):1055-238.

Lu et al., "Folate-targeted enzyme prodrug cancer therapy utilizing penicillin-V amidase and a doxorubicin prodrug," *J. Drug Target*, 7(1): 43-53 (1999).

Lu, J. Y. and Low, P. S., "Folate targeting of haptens to cancer cell surfaces mediates immunotherapy of syngeneic murine tumors," *Cancer Immunol Immunother*, 51: 153-162 (2002).

Lh, J.Y. and Low, P. S., "Folate-mediated delivery of macromolecular anticancer therapeutic agents." *Adv. Drug Del Rev.* 2002: 54(5): 675-693.

Mack D.O. et al., "The Carboxylation Activity of Vitamin K Analogs with Substitutions at Position 2 3 or 5 " *Journal of Biological Chemistry* ,1979: vol. 254 pp. 2656-2664.

Mancuso A.J. et al., "Activated Dimethyl Sulfoxide: Useful Reagents for Synthesis," *Synthesis*, 1981, pp. 165-184.

March, Advanced Organic Chemistry, 1992, John Wiley & Sons, 4th Ed., pp. 362-363, 816, 885, 896.

Mathias, C. J., "A kit formulation for preparation of [(111)In]In-DTPA-folate, a folate-receptor-targeted radiopharmaceutical." *Nucl. Med. Biol,.* 25(6): 585-587 (1998).

Matsui et al., "Studies on mitomycins. III. The synthesis and properties of mitomycin derivatives," *J Antibiot*, 21: 189-198 (1968).

Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.

McHugh M et al., "Demonstration of a High Affinity Folate Binder in Human Cell Membranes and Its Characterization in Cultured Human KB Cells," *J Biol Chem*, 1979; 254(22):11312-8.

Melani et al., "Targeting of interleukin 2 to human ovarian carcinoma by fusion with a single-chain Fv of antifolate receptor antibody." *Cancer Res.* 58(181: 4146-4154 (1998).

Melby, E.L. et al, "Entry of Protein Toxins in Polarized Epithelial Cells"; *Cancer Research*, 1993; 53: 1755-1760.

Mislick et al., "Transfection of folate-polylysine DNA complexes: evidence for lysosomal delivery," *Bioconiug. Chem.*, 6(5): 512-515 (1995).

Mock D.M. et al., "Urinary Biotin Analogs Increase in Humans During Chronic Supplementation: the Analogs are Biotin Metabolites," *Am J Physiol Endocrinol Metab*, 1997; 272: E83-E85.

Morshed et al., "Folate transport proteins mediate the bidirectional transport of 5- methyltetrahydrofolate in cultured human proximal tubule cells." *J. Nutr.*, 127(6): 1137-1147 (1997).

Nair et al., "Folate analogs altered in the C9-N10 bridge region. 14. 11-Oxahomofolic acid, a potential antitumor agent", *Journal of Medical Chemistry*, 23: 59-65 (1980).

Nair et al., "Folate analogs altered in the C9-N10 bridge region. 18. Synthesis and antitumor evaluation of 11-oxahomoaminopterin and related compounds," *Journal of Medical Chemistry*, 24: 1068-1073 (1981).

Nair et al., "Folate analogs altered in the C9-N10 bridge region: N10-tosylisohomofolic acid and N10-tosylisohomoaminopterin," *Journal of Medical Chemistry*, 21: 673-677 (1978).

Nair et al., "Folate analogs altered in the C9-N10 bridge region: 11-thiohomofolic acid," *Journal of Medical Chemistry.* 22: 850-855 (1979).

Nair et al., "Folate analogs. 20. Synthesis and antifolate activity of 1',2',3',4',5',6'-hexahydrohomofolic acid " *Journal of Medical Chemistry*, 26: 135-140 (1983).

Nair et al., "Folate analogs. 21. Synthesis and antifolate and antitumor activities of N10- (cyanomethy)-5.8-dideazafolic acid." *Journal of Medical Chemistry*. 26: 605-607 (1983).

Nair et al., "Folate analogs. 22. Synthesis and biological evaluation of two analogs of dihydrofolic acid possessing a 7,8-dihydro-8-oxapterin ring system," *Journal of Medical Chemistry*, 26: 1164-1168 (1983).

Nair et al., "Folate analogues altered in the C9-N10 bridge region. 10-Oxafolic acid and 10- oxaaminopterin." *Journal of Medical Chemistry*. 19: 825-829 (1976).

Neuss, N. et al., "Vinca Alkaloids. XXX (1). Chemistry Of The Deoxyvinblastines (Dcoxy-VLB), Leurosine (VLR), And Pleurosine, Dimeric Alkaloids From Vinca," *Tetrahedron Letters*, No. 7, pp. 783-787 (1968).

Neuzil J. et al., "Vitamin E Analogs: A New Class of Multiple Action Agents with Anti-Neoplastic and Anti-Atherogenic Activity," *Apoptosis*, 2002; vol. 7, pp. 179-187.

Nielsen P. et al., "Phosphates of Riboflavin and Riboflavin Analogs: A Reinvestigation by High-Performance Liquid Chromatography," *Analytical Biochemistry*, vol. 130, 1983, pp. 359-368.

Nishikawa, Yuji et al., "Growth Inhibition of Hepatoma Cells Induced by Vitamin K and Its Analogs " *Journal of Biological Chemistry*. 1995: vol. 270, No. 47, pp. 28304-28310.

Nosaka K.et al., "Separate Determination of Anticoccidial Thiamine Analogs by High-performance Liquid Chromatography," *ActaA Vitaminol. Et Enzymol*, 1984, vol. 6 (2), pp. 137-142.

Oatis et al., "Synthesis of quinazoline analogues of folic acid modified at position 10," *Journal of Medical Chemistry*, 20: 1393-1396 (1977).

Olsnes S. et al., "Immunotoxins-entry into cells and mechanisms of action," *Immunology Today*, 1989; vol. 10, No. 9, pp. 291-295.

Patrick et al., "Folate Receptors As Potential Therapeutic Targets in Choroid Plexus Tumors of Sv40 Transgenic Mice." *J. Neurooncol.*, 32(2): 111-123 (1997).

Patrick et al., "Intracerebral bispecific ligand-antibody conjugate increases survival of animals bearing endogenously arising brain tumors," *Int. J. Cancer*, 78(4): 470-79 (1998).

Peltier, Hillary M., et al., "The Total Synthesis of Tubulysin D," 2006, *J. Am. Chem. Soc.*, No. 128, pp. 16018-19.

Pizzorno G., et al., "Intracellular metabolism of 5,10-dideazatetrahydrofolic acid in human leukemia cell lines," *Molecular Pharmacology*, 1991, 39 (1), pp. 85-89.

Plante et al., "Polyglutamyl and polylysyl derivatives of the lysine analogues of folic acid and homofolic acid." *Journal of Medical Chemistry*, 19: 1295-1299 (1976).

Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.

Prabhu V. et al., "Arabidopsis dihydropteroate synthase: general properties and inhibition by reaction product and sulfonamides." *Phytochem.*, 1997. 45(1): 23-27.

Prasad et al., "Functional coupling between a bafilomycin A1-sensitive proton pump and a probenecid-sensitive folate transporter in human placental choriocarcinoma cells," *Biochim. Biophys. Acta*, 1994; 1222(2): 309.

Pratt, A.G. et al. "The Hydrolysis of Mono-, Di, And Triglutamate Derivatives Of Folic Acid With Bacterial Enzymes." *The Journal Of Biological Chemistry*,1968 vol. 243 No. 24 pp. 6367-6372.

Punj, V. et al., "Effect of Vitamin D Analog (1α Hydroxy D5) Immunoconjugated to Her-2 Antibody on Breast Cancer," *Int. J. Cancer*, 2004; 108: 922-929.

Raghavan B et al., "Cytotoxic Simplified Tubulysin Analogues," *J. Med. Chem.*, 2008; 51(6), pp. 1530-1533.

Ranasinghe, M. G. et al.; "A Facile Synthesis of Unsymmetrical Thiolsulfonates via Sulfonylation of Mercaptans," *Synthetic Communications*, 1988; 18(3), pp. 227-232.

Reddy et al., "Optimization of folate-conjugated liposomal vectors for folate receptor-mediated gene therapy." *J. Pharm. Sci.* 88(11): 1112-1118 (1999).

Reddy et al., "Preclinical evaluation of EC145, a folate-vinca alkaloid conjugate," *Cancer Res.*, 2007; 67:4434-42.

Reddy et al., "Retargeting of viral vectors to the folate receptor endocytic pathway," *J Control Release*. 74(1-3): 77-82 (2001).

Reddy, J. A., Low, P. S., "Folate-Mediated Targeting of Therapeutic and Imaging Agents to Cancers," *Crit. Rev. Ther. Drug Carrier Syst.*, vol. 15, No. 6, 1998, pp. 587-627.

Remington: The Science & Practice of Pharmacy, 21th Edition (Lippincott Williams & Wilkins, 2005).

Renz P. et al., "Synthesis of 4-Aza-5, 6-diethylbenzimidazole and Biosynthetic Preparation of 4- and 7-Aza-5, 6-dimethylbenzimidazolylcobamide," *Z. Naturforsch*, 1997, vol. 52c, pp. 287-291.

Rijnboutt et al., "Endocytosis of GPI-linked membrane folate receptor-alpha," *J. Cell Biol.*, 132(1-2): 35-47 (1996).

Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).

Roberts et al., "Folic acid analogs. Modifications in the benzene-ring region. 2. Thiazole analogs," *Journal of Medical Chemistry*. 15: 1310-1312 (1972).

Roberts et al., "Folic acid analogs. Modifications in the benzene-ring region. 1. 2'- and 3'-Azafolic acids." *Journal of Medical Chemistry*. 14: 125-130 (1971).

Roberts et al., "Folic acid analogs. Modifications in the benzene-ring region. 4. 3'-Ethyl- and 3'- isopropylfolic acids." *Journal of Medical Chemistry*. 17: 219-222 (1974).

Rose W.C., "Taxol-Based Combination Chemotherapy And Other In Vivo Preclinical Antitumor Studies," *J Natl Cancer Inst Monogr*, 1993, No. 15, pp. 47-53.

Ross et al., "Differential regulation of folate receptor isoforms in normal and malignant tissues in vivo and in established cell lines. Physiologic and clinical implications," *Cancer*, 73(9): 2432-2443, (1994).

Rothberg et al, "Cholesterol controls the clustering of the glycophospholipid-anchored membrane receptor for 5-methyltetrahydrofolate," *J. Cell Biol.*, 111(6): 2931-2938 (1990).

Rothberg et al., "The glycophospholipid-linked folate receptor internalizes folate without entering the clathrin-coated pit endocytic pathway," *J. Cell Biol.*, 110(3): 637-649 (1990).

Roy et al., "Targeting T cells against brain tumors with a bispecific ligand-antibody conjugate," *Int. J. Cancer* 76(5): 761-66 (1998).

Sadasivan et al., "The complete amino acid sequence of a human folate binding protein from KB cells determined from the cDNA." *J. Biol. Chem.*, 1989: 264: 5806-5811.

Sargent D.R. et al., "Antimetabolites of Pantothenic Acid, Ureido - and Carbamoyl-Derivatives," *Texas Reports on Biology and Medicine*. 1975, vol. 33. No. 3. pp. 433-443.

Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53. No. 9. pp. 879-885.

Scott J.M, "Preparation and Purification of Pteroic Acid from Pteroylglutamic Acid (Folic Acid)," *Methods In Enzymology*, 1980, vol. 66, pp. 657-660.

Search Report for Taiwan Patent Application No. 093101735, dated Jul. 14, 2007, 1 page.

Shimizu M. et al., "Synthesis and biological activities of new 1alpha, 25-dihydroxy-19-norvitamin D3 analogs with modifications in both the A-ring and the side chain," *Bioorganic & Medicinal Chemistry*, 2006; 14(12): 4277-94.

Shimizu, Kazui, et al., "Novel vitamin D3 antipsoriatic antedrugs: 16-En-22-oxa-1a,25-(OH)2D3 analogs," *Bioorganic & Medicinal Chemistry*, 2006;14: 1838-1850.

Shoup T.M. et al., "Synthesis of Fluorine-18-Labeled Biotin Derivatives: Biodistribution and Infection Localization." *J. Nucl. Med.*, 1994: 35: 1685-1690.

Skinner W.A. et al., "Structure-Activity Relations in the Vitamin F Series. II. Derivatives of α-Tocopherol Substituted at the 5-Methyl Group," *J. Med. Chem.*, 1969; 12 (1): 64-66.

Smart et al., "Clustered folate receptors deliver 5-methyltetrahydrofolate to cytoplasm of MA104 cells," *J. Cell Biol.*, 134(5): 1169-1177 (1996).

Smart et al., "Protein kinase C activators inhibit receptor-mediated potocytosis by preventing internalization of caveolae," *J. Cell Biol.*, 124(3): 307-313 (1994).

Spry C. et al., "A Class of Pantothenic Acid Analogs Inhibits Plasmodium Falciparum Pantothenate Kinase and Represses the Proliferation of Malaria Parasites," *Antimicrobial Agents and Chemotherapy*, 2005; 49(11): 4649-4657.

Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).

Steinmetz, H. et al., "Isolation, Crystal and Solution Structure Determination, and Biosynthesis of Tubulysins-Powerful Inhibitors of Tubulin Polymerization from Microbacteria", *Angew. Chem. Int. Ed.*, 2004, No. 43, pp. 4888-4892.

Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.

Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.

Takeda, K. et al., "A Synthesis of a New Type of Alkoxycarbonylating Reagents from 1,1-Bis[6- (trifluoromethyl)benzotriazolyl] Carbonate (BTBC) and Their Reactions," *Sythesis*, 1987; 6: 557-560.

Temple et al., "Synthesis of pseudo cofactor analogs as potential inhibitors of the folate enzymes," *Journal of Medical Chemistry*. 25: 161-166 (1982).

Theti, D. S. et al., "Selective delivery of CB300638, a cyclopenta[g]quinazoline-based thymidylate synthase inhibitor into human tumor cell lines overexpressing the alpha-isoform of the folate receptor." *Cancer Res.* 2003. 63(13): 3617-3618.

Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.

Trachewsky D., "Antihypertensive Effect of Riboflavin Analogs in Rats with Mineralocorticoid-Induced Hypertension," *Hypertension*, 1981; vol. 3, No. 1, pp. 75-80.

Truneh A. et al., "Temperature-sensitive differential affinity of TRAIL for its receptors. DR5 is the highest affinity receptor," *J Biol Chem*, 2000; 275(30):23319-25.

Turk et al., "Characterization of a novel pH-sensitive peptide that enhances drug release from folate-targeted liposomes at endosomal pHs." *Biochim Biophys Acta.* 1559(1): 56-68 (2002).

Ueda M. et al., "Effect of Vitamin B12 Derivatives on Urinary Excretion of Methylmalonic Acid in Liver Diseases." *Acta Med. Okayama.* 1970: vol. 24. pp. 365-372.

Varma, R. et al., "GPI-anchored proteins are organized in submicron domains at the surface," *Nature*, 394(6695): 798-801 (1998).

Verwey, J., "Mitomycin C-Induced Renal Toxicity, a Dose-Dependent Side Effect?," *Eur J Cancer Clin Onco*, 1987; vol. 23, No. 2, pp. 195-199.

Vesely D.L. et al., "Biotin Analogs Activate Guanylate Cyclase," *Molecular and Cellular Biochemistry*. 1984: vol. 60. pp. 109-114.

Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.

Vogel et al., "Peptide-Mediated Release of Folate-Targeted Liposome Contents From Endosomal Compartments," *J. Am. Chem. Soc.*, 1996; 118(7): 1581-1586.

Vyas D. et al., "A practical synthesis of mitomycin A and its analogs," *J Org Chem*, 1986; 31:4307-4309.

Wang S. et al., "Folate-mediated targeting of antineoplastic drugs, imaging agents, and nucleic acids to cancer cells." *J. Control Rel.* 1998: 53(1-3): 39-48.

Wang, Xiu-Fang et al., "Vitamin E Analogs Trigger Apoptosis in HER2/erbB2-Overexpressing Breast Cancer Cells by Signaling Via the Mitochondrial Pathway," *Biochemical and Biophysical Research Communication*, 2005; vol. 326, pp. 282-289.

Weinstock et al., "Folic acid analogs. II. p-{[(2,6-Diamino-8-purinyl)methyl]amino}-benzoyl-L-glutamic acid and related compounds " *Journal of Medical Chemistry*. 13: 995-997 (1970).

Weitman et al., "Cellular localization of the folate receptor: potential role in drug toxicity and folate homeostasis," *Cancer Res.*, 1992; 52(23): 6708-6711.

Weitman et al., "Distribution of the folate receptor GP38 in normal and malignant cell lines and tissues." *Cancer Res.*, 1992:52(12): 3396-3401.

Westerhof GR et al., "A photoaffinity analogue of folic acid as a probe for the identification and function of a membrane folate binding protein (mFBP) in human CCRF-CEM leukemia cells," *Proccedings of the American Association for Cancer Research*, 1991; 32:328.

Wiener et al., "Targeting dendrimer-chelates to tumors and tumor cells expressing the high-affinity folate receptor," *Invest. Radiol.* 32(12): 748-54 (1997).

Zimmer II. et al., "Potential anticancer agents V., Synthesis of folic acid and pteroic acid analogs derived of caffeine and theophylline." *Arzneimittelforschung*. 1966. 16(4), pp. 541-545.

Zimmerman, J., "Folic acid transport in organ-cultured mucosa of human intestine. Evidence for distinct carriers." *Gastroenterol.* 99(4): 964-972 (1990).

Angier, R. B., et al., "Pteroic Acid Analogs Containing Arsenic," J. American Chem. Soc., vol. 76, 1954, pp. 902-904.

Boothe, J. H., et al., "Pteroic Acid Derivatives. II. Pteroyl-γ-glutamylglutamic Acid and Pteroyl-γ-glutamyl-γ-glutamylglutamic Acid," J. American Chem. Soc., vol. 70, 1948, pp. 1099-1102.

Bartels R. et al., "Determination of pteroic acid by high-performance thin-layer chromatography: Contribution to the investigation of 7,8-dihydropteroate synthase," *Journal of Chromatography A*, 1994; vol. 659(1): 185-189 (abstract only).

Wikipedia, Derivative (Chemistry), http://en.wikipedia.org/wiki/Derivative_(chemistry), downloaded Dec. 16, 2009.

Wikipedia, Analog (Chemistry), http://en.wikipedia.org/wiki/Analog_(chemistry), downloaded Dec. 16, 2009.

Wikipedia, List of Purification Methods in Chemistry, http://en.wikipedia.org/wiki/List_of_purification_methods_in_chemistry, downloaded Dec. 16, 2009.

Wikipedia, Solution, http://en.wikipedia.org/wiki/Solution, downloaded Dec. 17, 2009.

Principles of Ion Exchange Chromatography, http://www.separations.us.tosohbioscience.com/ServiceSupport/TechSupport/ResourceCenter/PrinciplesofChromatography/IonExchange, downloaded Dec. 23, 2009.

Wikipedia, Conjugate, http://en.wikipedia.org/wild/Conjugate, downloaded Dec. 17, 2009.

Wikipedia, Complex (Chemistry), http://en.wikipedia.org/wiki/Complex_(chemistry), downloaded Dec. 23, 2009.

U.S. Appl. No. 12/666,712, filed Dec. 24, 2009, Leamon et al.

International Search Report for PCT/US2002/13045, dated Sep. 20, 2002.

Beevers, Christopher S., et al., "Curcumin Inhibits the Mammalian Target of Rapamycin-Mediated Signaling Pathways in Cancer Cells", 2006; *Int. Journal Cancer*; Vo. 119; pp. 757-764.

Brown, Nicole E., et al., "Delayed Cystogenesis and Increased Ciliogenesis Associated with th Re-Expression of Polaris in Tg737 Mutant Mice", 2003, *Kidney International*, vol. 63, pp. 1220-1229.

Bukanov Nikolay, O. et al., "Long-Lasting Arrest Of Murine Polycystic Kidney Disease With CDK Inhibitor Roscovitine", Dec. 14, 2006; *Nature*; vol. 444; pp. 949-952.

Hay, Nissim, et al., "Upstream and Downstream of mTOR", 2004, *Genes & Development*, vol. 18, No. 16, pp. 1926-1945.

Kennedy, Michael D., et al., "Evaluation of Folate Conjugate Uptake and Transport by the Choroid Plexus of Mice", (May 2003), vol. 20, No. 5, pp. 714-719.

Leamon, Christopher P., et al., "Folate-Liposome-Mediated Antisense Oligodeoxynucleotide Targeting to Cancer Cells: Evaluation in Vitro and in Vivo", 2003, *Bioconjugate Chemistry*, vol. 14, No. 4, pp. 738-747.

Nauta, Jeroen, et al., "Renal and Biliary Abnormalities in a New Murine Model of Autosomal Recessive Polycystic Kidney Disease", 1993, *Pediatr. Nephrol.* No. 7, pp. 163-172.

Piontek, Klaus B., et al. "A Functional Floxed Allele of Pkd1 that Can Be Conditionally Inactivated In Vivo", *J. Am. Soc. Nephrol.* vol. 15, pp. 3035-3043.

Shillingford, Jonathan M., et al., "The mTOR Pathway is Regulated by Polycystin-1, and its Inhibition Reverses Renal Cystogenesis in Polycyctic Kidney Disease", Apr. 4, 2006, *PNAS*. vol. 103, No. 14, pp. 5466-5471.

U.S. Appl. No. 60/590,580, filed Jul. 23, 2004, Vlahov et al.

Ke Cy et al., "Folate-Receptor-Targeting of Tn-111 Using Pteroic Acid Conjugates of Benzyl-DTPA and Benzyl-DOTA," J. Nucl. Med., 2004; 45(5):457P.

Regueiro-Ren et al., "Synthesis and Biological Activity of Novel Epothilone Aziridines," Organic Letters, 2001; vol. 3, No. 17: 2693-96.

Kamen et al., "A review of folate receptor alpha cycling and 5-methyltetrahydrofolate accumulation with an emphasis on cell models in vitro," Advanced Drug Delivery Reviews, 2004; vol. 56:1085-97.

Elnakat et al., "Distribution, functionality and gene regulation of folate receptor isoforms: implications in targeted therapy," Advanced Drug Delivery Reviews, 2004; vol. 56:1067-84.

Sabharanjak et al., "Folate receptor endocytosis and trafficking," Advanced Drug Delivery Reviews, 2004; vol. 56: 1099-1109.

Paulos et al., "Folate receptor-mediated targeting of therapeutic and imaging agents to activated macrophages in rheumatoid arthritis," Advanced Drug Delivery Reviews, 2004; vol. 56: 1205-17.

Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.

Lu et al., "Folate receptor-targeted immunotherapy of cancer: mechanism and therapeutic potential," Advanced Drug Delivery Reviews, 2004; vol. 56: 1161-76.

Antony, "Folate receptors: reflections on a personal odysssey and a perspective on unfolding truth," Advanced Drug Delivery Reviews, 2004; vol. 56: 1059-66.

Roy et al., "Folate-mediated targeting of T cells to tumors," Advanced Drug Delivery Reviews, 2004; vol. 56: 1219-31.

Ke et al., "Folate-receptor-targeted radionuclide imaging agents," Advanced Drug Delivery Reviews, 2004; vol. 56: 1143-60.

Gabizon et al., "Tumor cell targeting of liposome-entrapped drugs with phospholipid-anchored folic acid-PEG Conjugates," Advanced Drug Delivery Reviews, 2004; vol. 56: 1177-92.

Wikipedia, Structural analog, http://en.wikipedia.org/wiki/Structural_analog, downloaded Apr. 7, 2009.

Paulos CM et al., "Ligand Binding and Kinetics of Folate Receptor Recycling in Vivo: Impact on Receptor-Mediated Drug Delivery," Molecular Pharmacology, 2004; 66:1406-1414.

Griesser UJ, "The Importance of Solvents," in Polymorphism in the Pharmaceutical Industry, Hilfiker ed., 2006; p. 211-230.

Zhao et al., "Tumor-selective targeted delivery of genes and antisense oligodeoxyribonucleotides via the folate receptor," Advanced Drug Delivery Reviews, 2004; vol. 56: 1193-1204.

Wikipedia, Functional analog, http://en.wikipedia.org/wiki/Functional_analog, downloaded Apr. 7, 2009.

Wikipedia, Folic acid, http://en.wikipedia.org/wiki/Folic_acid, downloaded Apr. 7, 2009.

* cited by examiner

Pte (pteroic acid)

Pte-Glu (folic acid)

Synthesis of cy4-036 cy4-032

$C_{34}H_{66}N_6O_9 = 702$
Electrospray (+): M+H 703

(R = drug or drug-bearing moiety)

R₁, R₂ = H, alkyl, cycloalkyl or substituted phenyl
R₃-OH = drug or drug-bearing moiety

FOLATE MIMETICS AND FOLATE-RECEPTOR BINDING CONJUGATES THEREOF

This application claims the benefit of U.S. Provisional Application Ser. No. 60/286,082, filed Apr. 24, 2001, which is incorporated herein by reference in its entirety.

STATEMENT OF GOVERNMENT RIGHTS

This invention was made with Government support under Grant R01-CA70845 awarded by the National Institutes of Health—National Cancer Institute. The Government has certain rights in the invention.

FIELD OF THE INVENTION

This invention relates to folate mimetics and their use in therapeutic and diagnostic applications. More particularly, this invention relates to using des-glutamyl folic acid analogs recognized by and selectively bound by folate receptors and other folate binding proteins and the use of such analogs for targeted delivery of diagnostic or therapeutic agents to folate-receptor bearing cell populations.

BACKGROUND OF THE INVENTION

A number of methods are known for selectively targeting cells in a patient for delivery of diagnostic or therapeutic agents. Selective targeting has led to the introduction of various diagnostic agents for visualization of tissues, such as contrast agents useful in Magnetic Resonance Imaging (MRI), radiodiagnostic compositions, and the like. Introduction of therapeutic agents, such as compositions for radiotherapy or for neutron capture therapy, compositions for chemotherapy, various proteins, peptides, and nucleic acids, protein toxins, antisense oligonucleotides, liposomes, analgesics, antibiotics, antihypertensive agents, antiviral agents, antihistamines, expectorants, vitamins, plasmids, and the like, has also been demonstrated.

Folate conjugates have been used for the selective targeting of cell populations expressing folate receptors or other folate binding proteins to label or deliver bioactive compounds to such cells. The relative populations of these receptors and binding proteins have been exploited in achieving selectivity in the targeting of certain cells and tissues, such as the selective targeting of tumors expressing elevated levels of high-affinity folate receptors. The following publications, the disclosures of which are incorporated herein by reference, illustrate the nature and use of folate conjugates for diagnosis or delivery of biologically significant compounds to selected cell populations in patients in need of such diagnosis or treatment:

(a) Leamon and Low, "Cytotoxicity of Momordin-folate Conjugates in Cultured Human Cells" in *J. Biol. Chem.*, 1992, 267, 24966-24967.

(b) Leamon et al., "Cytotoxicity of Folate-pseudomonas Exotoxin Conjugates Towards Tumor Cells" in *J. Biol. Chem.*, 1993, 268, 24847-24854.

(c) Lee and Low, "Delivery of Liposomes into Cultured Kb Cells via Folate Receptor-mediated Endocytosis" in *J. Biol. Chem.*, 1994, 269, 3198-3204.

(d) Wang et al., "Delivery of Antisense Oligonucleotides Against the Human Epidermal Growth Factor Receptor into Cultured Kb Cells with Liposomes Conjugated to Folate via Polyethyleneglycol" in *Proc. Natl. Acad. Sci. U.S.A.*, 1995, 92, 3318-3322.

(e) Wang et al., "Synthesis, Purification and Tumor Cell Uptake of Ga-67-deferoxamine-folate, a Potential Radiopharmaceutical for Tumor Imaging" in *Bioconj. Chem.*, 1996, 7, 56-63.

(f) Leamon et al., "Delivery of Macromolecules into Living Cells: a Method That Exploits Folate Receptor Endocytosis" in *Proc. Natl. Acad. Sci., U.S.A.*, 1991, 88, 5572-5576.

(g) Krantz et al., "Conjugates of Folate Anti-Effector Cell Antibodies" in U.S. Pat. No. 5,547,668.

(h) Wedeking et al., "Metal Complexes Derivatized with Folate for Use in Diagnostic and Therapeutic Applications" in U.S. Pat. No. 6,093,382.

(i) Low et al., "Method for Enhancing Transmembrane Transport of Exogenous Molecules" in U.S. Pat. No. 5,416,016.

(j) Miotti et al., "Characterization of Human Ovarian Carcinoma-Associated Antigens Defined by Novel Monoclonal Antibodies with Tumor-Restricted Specificity" in *Int. J. Cancer*, 1987, 39, 297-303.

(k) Campell et al., "Folate-Binding Protein is a Marker for Ovarian Cancer" in *Cancer Res.*, 1991, 51, 5329-5338.

(l) Jansen et al., "Identification of a Membrane-Associated Folate-Binding Protein in Human Leukemic CCRF-CEM Cells with Transport-Related Methotrexate Resistance" in *Cancer Res.*, 1989, 49, 2455-2459.

Multiple types of folate recognition sites present on cells, such as α-folate receptors, β-folate receptors, folate binding proteins, and the like, have been shown to recognize and bind the conjugates described above. The primary pathway for entry of folate derivatives into cells is through a facilitated transport mechanism mediated by a membrane transport protein. However, when folate is covalently conjugated to certain small molecules and macromolecules, the transport system can fail to recognize the folate molecule.

Advantageously, in addition to the facilitated transport protein, some cells possess a second membrane-bound receptor, folate binding protein (FBP), that allows folate uptake via receptor-mediated endocytosis. At physiological plasma concentrations (nanomolar range), folic acid binds to cell surface receptors and is internalized via an endocytic process. Receptor-mediated endocytosis is the movement of extracellular ligands bound to cell surface receptors into the interior of the cells through invagination of the membrane, a process that is initiated by the binding of a ligand to its specific receptor. The uptake of substances by receptor-mediated endocytosis is a characteristic ability of some normal, healthy cells such as macrophages, hepatocytes, fibroblasts, reticulocytes, and the like, as well as abnormal or pathogenic cells, such as tumor cells. Notably, folate binding proteins involved in endocytosis are less sensitive to modification of the folate molecule than the membrane transport proteins, and often recognize folate conjugates. Both targeting and uptake of conjugated diagnostic and therapeutic agents are enhanced.

Following endosome acidification, the folate receptor changes conformation near its ligand-binding domain and releases the folic acid molecule. Folate receptors are known to recycle back to the membrane surface for additional rounds of ligand-mediated internalization. However, a significant fraction of the internalized receptor-folic acid complex has been shown to return back to the cell surface shortly after endocytosis. This suggests that the acid-triggered ligand release mechanism does not proceed to completion, at least after the first round of internalization (Kamen et al., 1988, *J. Biol. Chem.* 263, 13602-13609).

Pteroic acid, which is essentially folic acid lacking the distal glutamyl residue (FIG. 1), does not bind to the high-affinity folate receptor to any appreciable extent (Kamen et al., 1986, *Proc. Natl. Acad. Sci., U.S.A.* 83, 5983-5987); in fact, 2 µM pteroic acid (100-fold excess) had absolutely no effect on the binding of folate to the folate receptor. Thus, the glutamyl residue of folic acid, or some portion thereof, was generally thought to be required for efficient, specific receptor recognition. However, recent studies have revealed that the glutamyl residue of folic acid could be replaced with a lysyl residue without disturbing the binding affinity of the ligand (McAlinden et al., 1991, *Biochemistry* 30, 5674-5681.; Wu et al., 1997, *J. Membrane Biol.* 159, 137-147), that the glutamyl residue can be replaced with a glycyl residue without substantially altering cellular uptake, and that no selective isomeric (i.e., α-glutamyl vs. γ-glutamyl) conjugation requirement necessarily exists (Leamon et al., *J. Drug Targeting* 7:157-169 (1999); Linder et al., *J. Nuclear Med.* 41(5): 470 Suppl. 2000).

Efforts to improve the selectivity of targeting or increase the diversity of the agents delivered to the cell or tissue have been hampered by a number of complications, including the complex syntheses required for the preparation of these conjugates. Such synthetic schemes are not only time consuming, but may also preclude the use of certain conjugates due to synthetic incompatibilities. A folic acid analog capable of expanding the number or diversity of agents, via the conjugates of such agents and these folic acid analogs, presentable to target cells would be advantageous.

SUMMARY OF THE INVENTION

The present invention provides a compound that is capable of binding as a ligand to a folate recognition site. The compound is referred to as a "non-peptide folic acid analog."

The present invention also provides a ligand-agent conjugate capable of binding to a folate recognition site, the ligand-agent conjugate comprising a diagnostic or therapeutic agent in association with a non-peptide folic acid analog.

The present invention also provides a ligand-agent conjugate capable of binding to a folate recognition site with high affinity, the ligand-agent conjugate comprising a diagnostic or therapeutic agent in association with a plurality of non-peptide folic acid analogs.

The present invention also provides a method for targeting a cell or tissue with a diagnostic or therapeutic agent, comprising the step of administering to a patient an effective amount of a ligand-agent conjugate comprising a diagnostic or therapeutic agent in association with a non-peptide folic acid analog.

DETAILED DESCRIPTION OF THE PREFERRED EMBODIMENTS

The present invention provides a ligand capable of binding to a folate recognition site, comprising a non-peptide folic acid analog of general formula

I:

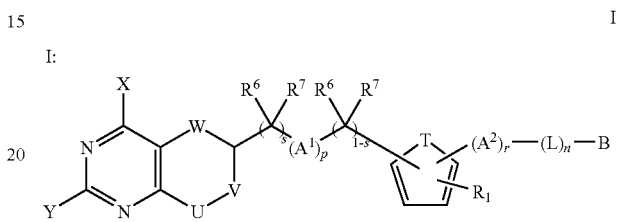

wherein

X and Y are each independently selected from the group consisting of halo, $R^2$, $OR^2$, $SR^3$, and $NR^4R^5$;

U, V, and W represent divalent moieties each independently selected from the group consisting of —$(R^{6'})C$=, —N=, —$(R^{6'})C(R^{7'})$—, and —$N(R^{4'})$—;

T is selected from the group consisting of S, O, N and —C=C— such that the ring structure of which T is a member is aromatic;

$A^1$ and $A^2$ are each independently selected from the group consisting of —C(Z)—, —C(Z)O—, —OC(Z)—, —$N(R^{4''})$—, —C(Z)—$N(R^{4''})$—, —$N(R^{4''})$—C(Z)—, —O—C(Z)—$N(R^{4''})$—, —$N(R^{4''})$—C(Z)—O—, —$N(R^{4''})$—C(Z)—$N(R^{5''})$—, —O—, —S—, —S(O)—, —$S(O)_2$—, —$N(R^{4''})S(O)_2$—, —$C(R^{6''})(R^{7''})$—, —N(C=CH)—, —$N(CH_2$—C=CH)—, $C_1$-$C_{12}$ alkyl and $C_1$-$C_{12}$ alkoxy; where Z is oxygen or sulfur;

$R^1$ is selected from the group consisting of hydrogen, halo, $C_1$-$C_{12}$ alkyl, and $C_1$-$C_{12}$ alkoxy;

$R^2$, $R^3$, $R^4$, $R^{4'}$, $R^{4''}$, $R^5$, $R^{5''}$, $R^{6''}$ and $R^{7''}$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or, $R^6$ and $R^7$ are taken together to form O=;

$R^{6'}$ and $R^{7'}$ are each independently selected from the group consisting of hydrogen, halo, $C_1$-$C_{12}$ alkyl, and $C_1$-$C_{12}$ alkoxy; or, $R^{6'}$ and $R^{7'}$ are taken together to form O=;

L is a divalent linker;

n, p, r and s are each independently either 0 or 1; and

B is hydrogen or a leaving group;

provided that the linker L does not include a naturally occurring amino acid covalently linked to $A^2$ at its α-amino group through an amide bond. It should be understood that the structure of formula I includes tautomeric structures, for example in compounds where X is OH, SH or NH.

In the compound of the invention wherein any one or more of $A^1$, $A^2$, $R^1$, $R^2$, $R^3$, $R^4$, $R^{4'}$, $R^{4''}$, $R^5$, $R^{5''}$, $R^{6''}$, $R^{7''}$, $R^6$, $R^7$, $R^{6'}$ and $R^{7'}$ comprises an alkyl, alkoxy, alkylamino, alkanoyl, alkenyl, alkynyl, alkoxy carbonyl, or alkylamino carbonyl group, the group preferably contains 1 to 6 carbon atoms ($C_1$-$C_6$); more preferably it contains 1 to 4 carbon atoms ($C_1$-$C_4$).

Figure 1:
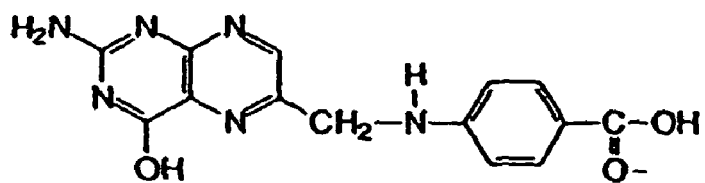
FIG. 1 is a schematic representation of folic acid and pteroic acid.
Figure 1:
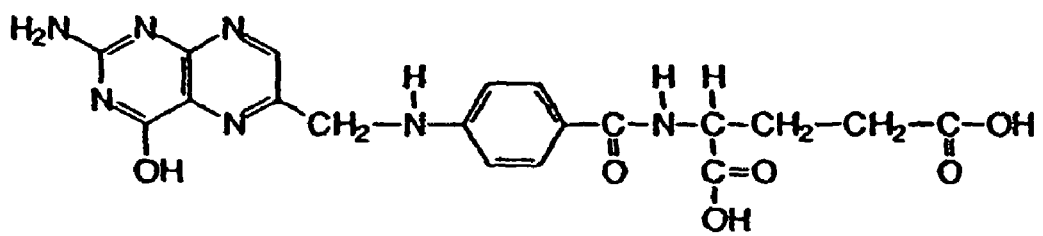

Folic acid contains a glutamyl residue bound at its α-amino group via an amide bond to the benzoate moiety of pteroic acid (FIG. 1). This amide bond would typically not be classified as a "peptide" bond because pteroic acid is not an amino acid; a peptide bond is typically characterized as a bond in which the carboxyl group of one amino acid is condensed with the amino group of another to form a —CO.NH— linkage.

Nonetheless, for ease of reference, the compound of formula I, which is defined as having linker L that lacks a glutamyl or any other naturally occurring amino acid residue covalently linked to $A^2$ at its α-amino group through an amide bond, is termed herein a "non-peptide" folic acid analog. That is, the term "non-peptide" as used herein in reference to the compound of formula I, means that linker L does not include a naturally occurring amino acid covalently linked to $A^2$ through an amide bond at its α-amino group, thereby distinguishing the compound of formula I from, for example, folic acid, pteroyl-γ-glutamate-cysteine, pteroyl-α-glutamate-cysteine, and pteroyl-glycine-cysteine (Leamon et al., *J. Drug Targeting* 7:157-169 (1999)). In a preferred embodiment of the non-peptide folic acid analog of the invention, linker L does not include any amino acid (whether naturally occurring or non-naturally occurring) covalently linked to $A^2$ through an amide bond at its α-amino group.

It should be further understood that the compound of formula I can contain a naturally occurring amino acid covalently linked to $A^2$ at a site other than its α-amino group, a non-naturally occurring amino acid covalently linked to $A^2$ through an amide bond or otherwise, as well as any other non-amino acid moiety covalently linked to $A^2$ through an amide bond or otherwise, as defined with reference to the formula.

The general chemical terms used in the formulae above have their usual meanings. For example, the term "alkyl" as used herein refers to a linear or branched chain of carbon atoms, such as methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

The term "alkoxy" as used herein refers to alkyl, as defined above, substituted with oxygen, such as methoxy, ethoxy, propoxy, isopropoxy, butoxy, tert-butoxy and the like.

The term "alkanoyl" as used herein refers to formyl, or alkyl, as defined above, terminally-substituted with a carbonyl such as acetyl, propanoyl, butanoyl, pentanoyl and the like.

The term "alkenyl" as used herein refers to a linear or branched chain of carbon atoms with one or more carbon-carbon double bonds, such as vinyl.

The term "alkynyl" as used herein refers to a linear or branched chain of carbon atoms with one or more carbon-carbon triple bonds.

The term "alkylamino" as used herein refers to alkyl, as defined above, substituted with nitrogen, including both monoalkylamino such as methylamino, ethylamino, propylamino, tert-butylamino, and the like, and dialkylamino such as dimethylamino, diethylamino, methylpropylamino, and the like.

The term "halo" as used herein refers to any Group 17 element and includes fluoro, chloro, bromo, iodo, and astatine (o).

The term "alkylenyl" as used herein refers to a divalent linear or branched chain of carbon atoms such as methylene, ethylene, 2-methylpropylene, and the like.

The term "leaving group" as used herein refers to a functionality that may be replaced, such as an activated halo or alkoxy, by an introduced substituent, such as a alkylamino, carbon nucleophile, a different alkoxy, a different halo, and the like.

The term "naturally occurring amino acid" as used herein refers to the 20 coded amino acids available for endogenous protein synthesis, such as glycine, alanine, methionine, and the like.

A preferred embodiment of the ligand is one having the general formula I wherein p is 1, s is 1, and T, U, V, W, X, Y, $R^1$, $R^6$, $R^7$ and $A^1$ are selected such that at least a portion of the molecule is isosteric with pteroic acid. By "isosteric" it is meant that the two compounds or portions of compounds comprise isosteric substituents that occupy similar volumes and, preferably but not necessarily, have similar electronic character. As a nonlimiting example, hydrogen, halo, $CH_3$, OH, SH and $NH_2$ may be considered for purposes of this invention as being isosteric substituents.

Folate receptor activity is expected to be retained when isosteric substitutions are made to that portion of the non-peptide folic acid analog that is derived from pteroic acid. For example, as reported in Jansen, "Receptor- and Carrier-Mediated Transport Systems for Folates and Antifolates," in *Anticancer Drug Development Guide: Antifolate Drugs in Cancer Therapy*, Jackman, Ed., Humana Press Inc, Totowa N.J. (1999), ring substituents X and Y, ring components U, V, W, T, and $A^1$ can be substituted in the pteroic acid reference structure while in most cases retaining folate receptor affinity.

An example of a preferred ligand according to the invention having a portion that is isosteric with pteroic acid is a ligand having formula I (including tautomers thereof) wherein X and Y are each independently selected from the group consisting of hydrogen, halo, $CH_3$, OH, SH and $NH_2$, with X more preferably being OH;

U, V and W represent divalent moieties each independently selected from the group consisting of —CH= and —N=;

$A^1$ is selected from the group consisting of —C(Z)—, —NH—, —N($CH_3$)—, —O—, —S—, —S(O)—, —S(O)$_2$—, —$CH_2$—, —CH($CH_3$)—, —C($CH_3$)$_2$—, —N($CH_2$—C≡CH)— and —N(C≡CH)—; where Z is oxygen or sulfur;

$R^1$ is selected from the group consisting of hydrogen, halo and methyl;

$R^6$ and $R^7$ are each independently selected from the group consisting of hydrogen, halo, $CH_3$, OH, SH and $NH_2$; or, $R^6$ and $R^7$ are taken together to form O=;

$A^2$ is selected from the group consisting of —C(Z)—, —C(Z)O—, —OC(Z)—, —N($R^{4''}$)—, —C(Z)—N($R^{4''}$)—, —N($R^{4''}$)—C(Z)—, —O—C(Z)—N($R^{4''}$)—, —N($R^{4''}$)—C(Z)—O—, —N($R^{4''}$)—C(Z)—N($R^{5''}$)—, —O—, —S—, —S(O)—, —S(O)$_2$—, —N($R^{4''}$)S(O)$_2$—, —C($R^{6''}$)($R^{7''}$)—, $C_1$-$C_6$ alkyl; $C_1$-$C_6$ alkoxy; where Z is oxygen or sulfur;

p and r are each 1; and

T, $R^{4''}$, $R^{5''}$, $R^{6''}$, $R^{7''}$, L, n, s and B are as defined above; provided that the linker L does not include a naturally occurring amino acid covalently linked to $A^2$ at its α-amino group through an amide bond. More preferably, T is —C=C—.

A particularly preferred ligand of the invention is a derivative of pteroic acid and has formula I (including tautomers thereof) wherein X is OH; Y is $NH_2$; U and W are each —N=; V is —CH—; T is —C=C—; $A^1$ is —NH—; $R^1$ is hydrogen; $A^2$ is —C(O)—, —C(O)O—, or —C(O)NH— and is para to $A^1$; $R^6$ and $R^7$ are hydrogen; p, r and s are each 1; and L, n and B are as defined elsewhere herein; provided that the linker L does not include a naturally occurring amino acid covalently linked to $A^2$ at its α-amino group through an amide bond.

One embodiment of the invention is a ligand capable of binding to a folate recognition site, such as a folate binding protein, folate receptor, and the like. Such a non-peptide folate analog may also be described as a folate mimetic. Compounds illustrative of this embodiment are selected from the general formula I. Such analogs may operate as surrogates for folate in methods utilizing folate, such as targeting molecules for cells or tissues expressing folate recognition sites.

In a particularly preferred embodiment, the compound of the invention has formula I and further exhibits binding affinity for a folate receptor. A relative binding affinity assay is described in detail in Example IV and in Westerhoff et al. (Mol. Pharm., 1995, 48:459-471). Performing this assay is straightforward. A preferred compound exhibits a binding affinity for the folate receptor relative to folic acid of at least about 0.01, more preferably at least about 0.05, even more preferably at least about 0.10, even more preferably at least about 0.25, even more preferably at least about 0.50, and most preferably at least about 0.75, wherein the binding affinity of folic acid for the folate receptor is defined as 1.0. It should be understood that the binding affinity of the compound of the invention may exceed 1.0, in cases where the binding affinity of the compound for the folate receptor is greater than that of folic acid itself.

The compounds of formula I may optionally include a linker, spacer, or couple of variable length. The linker, spacer, or couple, hereinafter collectively referred to as a "linker," is adapted for connecting the folate analog to another molecule in other embodiments of the invention. A divalent linker L is present in the folate analog of formula I when the integer n is equal to 1. Such linkers are known in the art and are often used to "associate" one chemical entity to another. As used herein, the term "association" refers to any manner of coexistence of two or more molecules, such as complexation, chelation, ion-pairing, covalent bonding, and the like, such that for a time sufficient to administer the associated molecules, the associated molecules may be interpreted as a single entity.

The linker may create either a permanent or a semipermanent (i.e., labile) linkage. The inclusion of a semipermanent linkage is especially advantageous for applications in which cellular uptake of the drug is desired. The ability to form a bioactive conjugate utilizing a linkage other than a peptide linkage (e.g., the glutamyl linkage of typical folate conjugates) provides an important degree of chemical flexibility for the linkage of the pteroic acid moiety to the drug payload. The capacity of a target cell for uptake of a folate-drug conjugate is expected to be dramatically increased when a linkage is selected that promotes drug release from the conjugate by exploiting known endosomal hydrolytic or reductive mechanisms (i.e., molecular separation between the drug payload and the ligand).

A preferred embodiment of the ligand-agent conjugate of the invention therefore includes a linker whereby a cell targeting ligand (i.e., the non-peptide folic acid analog) is chemically coupled to a drug molecule via a linker that is designed to be metabolized within the endosomal milieu. Following extracellular receptor binding and endocytic entry of the drug conjugate, endosome factors are expected to hydrolytically or reductively cleave the linker moiety of the conjugate, thereby facilitating release of the drug from the ligand. This process is depicted below:

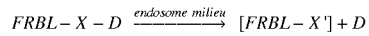

wherein the abbreviations are as follows: FRBL, folate receptor binding ligand; X, endosome-cleavable linker; D, drug moiety; X', linker fragment.

A preferred semi-permanent linker thus includes a functionality, such as a disulfide, ester, other hydrolyzable group, and the like, that allows separation of the ligand and the agent once the conjugate has reached the treatment site.

Semi-permanent linkers preferably depend upon endogenous mechanisms of cleavage, and include metabolically labile linkers, such as a nucleotide, amide, ester, and the like subject to cleavage by peptidases, esterases, phosphodiesterases, reductases, and the like, which provides a stable ligand-agent conjugate prior to delivery but allows cleavage upon reaching the target or treatment site. Preferred linkers used to produce these drug conjugates are biologically labile (pH sensitive, redox sensitive, enzymatically sensitive) such that the ligand-receptor complex can be separated from the macromolecule "payload" in a predetermined manner (e.g., following endocytosis). The inclusion of a metabolically labile function is advantageously chosen in an end-use dependent manner such that following the binding of the conjugate, or additionally subsequent uptake of the conjugate as described below, the metabolically labile association may be cleaved thus releasing the agent from the ligand, either locally (extracellularly) in the case of binding of the conjugate to the cell surface, or intracellularly, as in the case of post-uptake by the cell.

The divalent linker L comprises a linear or branched chain comprising a plurality of linking groups $L_1, L_2, \ldots, L_m$, wherein "m" is an integer from 0 to about 50. Preferably, m is selected such the number of atoms in the linear backbone of linker L is at least about 1, more preferably at least about 3, most preferably at least about 6; and at most about 100, more preferably at most about 50, and most preferably at most about 20.

Each linking group "$L_m$" is also a divalent moiety composed of atoms selected from the group consisting of carbon, nitrogen, oxygen, and sulfur, providing that an oxygen atom is not adjacent to another oxygen or sulfur atom, except when the sulfur atom is oxidized, as in —S(O)$_2$—. Each individual linking unit "$L_m$" can be the same or different and is thus independently selected from the group of divalent radicals. Illustrative divalent radicals are —CR$^{6''}$R$^{7''}$—, —(R$^{6''}$)C=C(R$^{7''}$)—, —CC—, —C(O)—, —O—, —S—, —SO$_2$—, —N(R$^{3''}$)—, —(R$^{6''}$)C=N—, —C(S)—, —P(O)(OR$^{3''}$)—, —P(O)(OR$^{3''}$)O—, and the like.

R$^{3''}$ is a group suitable for nitrogen or oxygen attachment, such as hydrogen, $C_1$-$C_4$ alkyl, $C_2$-$C_4$ alkenyl, $C_3$-$C_8$ cycloalkyl, aryl, $C_1$-$C_4$ alkanoyl, acryloyl, and the like. R$^{3''}$ attached to nitrogen may also be hydroxy, $C_1$-$C_4$ alkoxy, amino, monoalkylamino, or dialkylamino. It is appreciated that R$^{3''}$ may be selected independently for each linking group $L_m$.

R$^{6''}$ and R$^{7''}$ are each independently selected from groups suitable for carbon attachment such as hydrogen, $C_1$-$C_4$ alkyl, $C_2$-$C_4$ alkenyl, hydroxy, halo, $C_1$-$C_4$ alkoxy, $C_3$-$C_8$ cycloalkyl, aryl, $C_1$-$C_4$ alkanoyl, acryloyl, and the like. In addition, R$^{6''}$ and R$^{7''}$ are selected independently for each linking group $L_m$.

The linker L may also possess one or more cyclic regions, wherein a subset of the linking groups "$L_m$" form one or more rings, including, but not limited to divalent cycloalkyl, such as cyclopent-1,3-diyl, cyclohex-1,1-diyl, and the like; divalent heterocyclyl, such as pyrrolidin-1,3-diyl, piperidin-2,2-diyl; and divalent aromatic groups, such as 1,3-phenylene, pyrrol-1,2-diyl, and the like.

Illustrative linkers L are polyalkylenes, polyalkylene glycols such as polyethylene glycol (PEG), N-(2-hydroxypropyl)methacrylamide (HPMA), and the like. Other examples of such linkers may be found in U.S. Pat. Nos. 6,207,157, 6,184,042, 6,177,404, 6,171,859, and 6,171,614, the disclosures of which are incorporated herein by reference. The invention is not intended to be limited by the nature or length of the linker L.

The term "alkenyl" as used herein refers to a linear or branched chain of carbon atoms, such as ethenyl, propenyl, 2-methylethenyl, and the like.

The term "cycloalkyl" as used herein refers to a cyclic chain of carbon atoms, such as cyclopropyl, cyclopentyl, cyclohexyl, and the like.

The term "aryl" as used herein refers to an aromatic moiety, such as phenyl, pyridinyl, pyrimidinyl, and the like. The aryl group is optionally substituted with from 1 to 3 substituents, such as with halo, alkyl, alkoxy, as defined above, and the like.

The term "acryloyl" as used herein refers to aryl, as defined above, substituted with a carbonyl group, such as benzoyl, picolinyl, and the like.

The term "polyalkylene" as used herein refers to polymers of alkenes, such as polyethylene, polypropylene, and the like.

Synthesis of non-peptide folic acid analogs may be accomplished by methods known to the skilled artisan. In addition, the optional incorporation of a linker may also be accomplished by methods known to the skilled artisan.

The present invention also provides a ligand-agent conjugate capable of binding to a folate recognition site, comprising a diagnostic or therapeutic agent in association with a non-peptide folic acid analog of general formula II:

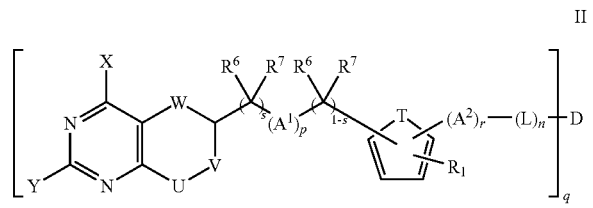

where

X, Y, U, V, W, T, $A^1$, $A^2$, $R^1$, $R^6$, $R^7$, L, n, p, r and s are as defined above;

q is an integer $\geq 1$; and,

D is a diagnostic agent or a therapeutic agent.

One embodiment of the invention is a ligand-agent conjugate capable of binding to a folate recognition site, such as a folate binding protein, folate receptor, and the like. Compounds illustrative of this embodiment are selected from the general formula II, where the integer q is equal to 1. Such analogs may operate as a means for targeting of and delivery to cells or tissues expressing folate recognition sites. The compounds of formula II may optionally include a linker L, where L is as defined above and where the integer n is equal to 1.

Another embodiment of the present invention is a ligand-agent conjugate capable of binding to a folate recognition site with high affinity, comprising a diagnostic or therapeutic agent in association with a plurality of non-peptide folic acid analogs of general formula II, where the integer q is 2 or greater. Similarly, such ligand-agent conjugates may optionally comprise a plurality of ligands each possessing a linker L, where L is as defined above and where the integer n is equal to 1. Such conjugates possessing a plurality of folate analogs in association with the diagnostic or therapeutic agent may advantageously enhance recognition of the conjugate by the recognition site.

The diagnostic or therapeutic agent D can be linked to the ligand at $(L)_n$ by any type of molecular interaction including a covalent bond, and ionic bond or association, hydrogen bonding or other type of complexation to form the ligand-agent conjugate.

Synthesis of ligand-agent conjugates may be accomplished by methods known to the skilled artisan depending upon the nature of the association of the ligand and the agent.

Virtually any type of molecule (small molecular weight chemotherapeutic, peptide, protein, oligosaccharide, antisense oligonucleotide, plasmid, ribozyme, artificial chromosome, micelle, liposome, etc.) can be more efficiently delivered into cells using this technology.

Diagnostic agents useful in the present invention include compounds capable of labeling a cell or tissue with a contrast agent for the generation or modulation of signal intensity in biomedical imaging. Such contrast agents may be used for imaging such cells and tissues using techniques such as Magnetic Resonance Imaging (MRI), radio-imaging, radio-diagnosis, and the like. Such labeling of the cell or tissue is illustratively accomplished by incorporation of superparamagnetic, paramagnetic, ferrimagnetic, or ferromagnetic metals, radioactive gamma-emitting, positron-emitting or photon-emitting metals, radionuclides, other radioactive elements such as certain halogen isotopes (radiohalogens), and the like, in the agent. The diagnostic agent may be a chelating agent capable of binding such metals described above, or a radio-pharmaceutical possessing an organic fragment, such as an aromatic ring, possessing a radiohalogen. Such chelating agents are known to the skilled artisan.

Metals useful in the invention employing such chelating agents for MRI include certain ions of chromium, manganese, iron, cobalt, nickel, copper, praseodymium, neodymium, samarium, gadolinium, terbium, dysprosium, holmium, erbium, ytterbium, and the like, such as Cr(III), Mn(II), Fe(II), Fe(III), and Ni(II). Metals useful in the invention employing such chelating agents for radio-imaging include certain isotopes of gallium, indium, copper, technetium, rhenium, and the like, such as $^{99m}$Tc, $^{51}$Cr, $^{67}$Ga, $^{68}$Ga, $^{103}$Ru, $^{211}$Bi, $^{64}$Cu and $^{111}$In. Radiobalogens useful in the invention employing radio-pharmaceuticals include certain isotopes of fluorine, iodine, astatine, and the like, such as $^{18}$F, $^{123}$I, and $^{131}$I.

Visualization techniques suitable for radioimaging are known in the art, such as positron emission tomography (PET), planar or SPECT imaging, gamma cameras, scintillation, and the like.

Therapeutic agents useful in the present invention include compounds capable of modifying, modulating, or otherwise altering certain cellular or tissue functions. Therapies include elimination of certain pathogenic cell populations or pathogenic tissues, enhancing beneficial functions in host cells or host tissues, protecting host cells or host tissues from non-selective treatment, and the like.

One embodiment of the invention is a ligand-therapeutic agent conjugate wherein the therapeutic agent targets pathogenic cells or tissues, such as tumors, bacteria, and the like. Such therapeutic agents include chemotherapeutic agents, antimicrobial agents, or other cytotoxic agents associated with the targeting ligand. Such cytotoxic agents, may lead to the destruction of the pathogenic cell or tissue. The therapeutic agent may be a radiotherapeutic agent. These agents, like the related diagnostic agents above, may possess a chelating functionality capable of sequestering a radionuclide, such as a radioactive metal or a radioactive alpha or beta-emitting metal suitable for nuclear medicine, or alternatively a suitable functionality bearing a radiohalogen, such as an aryl group. In this context however, the metal or halogen is used for radiotherapy rather than for radiodiagnosis. Metals appropriate for such radiotherapeutic agents are known in the art, including certain isotopes of gadolinium, technetium, chromium, gallium, indium, ytterbium, lanthanum, yttrium, samarium, holmium, dysprosium, copper, ruthenium, rhenium, lead, bismuth, and the like, such as $^{157}Gd$, $^{64}Cu$, $^{67}Cu$, $^{186}Re$, $^{188}Re$, $^{90}Y$, $^{111}In$, and $^{177}Lu$. Radiohalogens are also useful in the invention for radiotherapeutic agents, including certain isotopes of iodine, astatine, and the like, such as $^{125}I$, $^{131}I$, and $^{211}At$. In another embodiment, the therapeutic may be a species suitable for neutron capture therapy, such as an organoborane moiety, comprising $^{10}B$.

Chemotherapeutic agents useful in the present invention include certain alkylating agents, such as busulfan, carboquone, chlomaphazine, lomustine, tubercidin, and the like, certain antimetabolites, such as fludarabine, doxifluridine, and the like, certain steroids and steroid analogs, such as calusterone, testolactone, flutamide, tamoxifen, hexestrol, melengestrol, and the like, certain antiadrenals, such as mitolane, and the like, certain LH-RH analogs, such as buserelin, leuprolide, and the like, and certain anti-angiogenic agents.

Another embodiment of the invention is therapeutic ligand-agent conjugate that targets cells or tissue, such that a beneficial function of the targeted cell or tissue is enhanced by the therapeutic agent, such as an inflammatory, pro-inflammatory, or anti-inflammatory agent, antibiotic, analgesic, antiviral agent, and the like. Still other therapeutic agents useful in the present invention may protect a targeted cell or tissue from a subsequent non-selective treatment targeted to a different pathogenic cell or tissue, such as an immunosuppressant.

The present invention also provides a method for delivering a diagnostic or therapeutic agent to a targeted cell population. An effective amount of a ligand-agent conjugate comprising a diagnostic or therapeutic agent in association with a non-peptide folic acid analog of general formula II, where the integer q is 1 or greater, is delivered to the targeted cell population. The targeted cells possess a folate receptor to which the ligand-agent conjugate binds. The ligand thus selectively targets a certain cell or tissue, by binding to the receptors or proteins present in such cells or tissues that recognize the folic acid and folic acid analogs. If desired, a plurality of non-peptide folate analog conjugates can be administered.

In one embodiment of the method of the invention, the diagnostic or therapeutic effect is achieved as a direct or indirect result of binding of the ligand-agent conjugate to the folate receptor on the cell surface (i.e., "docking"). For example, in vivo biomedical imaging can be facilitated whether or not the diagnostic agent is internalized, and in some instances, for example in the case of a cytotoxic diagnostic agent, it is preferable that the diagnostic agent remain outside the cell. As another example, the therapeutic agent can include an immune stimulating factor such as an antigen, which is preferably retained on the extracellular surface on the cell.

In another embodiment of the method of the invention, the diagnostic or therapeutic effect is achieved as a result of uptake or internalization of the therapeutic or diagnostic agent via binding to the folate receptor followed by internalization of the receptor-ligand complex. It is appreciated that the method of the invention is suitable for effecting uptake by cells or tissue of ligand-agent conjugates, where the agent is a molecule or compound that would otherwise exhibit poor uptake by the cell or tissue by active transport, diffusion, or other passive transport.

The targeted cell population can be endogenous to exogenous to the patient. For example, it can be an endogenous population comprising a somatic or tumor cell population in a patient, a cancerous cell population, an organ, tissue or bodily fluid, or a virus-infected cell population. The ligand-agent conjugate can be delivered to a patient locally or systemically. For example, the conjugate can be delivered parenterally by intramuscular, intravenous or subcutaneous injection; likewise it can be formulated for oral administration.

An exogenous population of cells can include an ex vivo or in vitro population of cells. For example, the target cell population can be an ex vivo population of cells such as bone marrow cells, stem cells, or cells of an organ or tissue that have been removed from the patient's body. The ex vivo cells are contacted with the ligand-agent conjugate of the invention and subsequently returned to the body of the patient. Gene therapy, for example, can be accomplished using a ligand-agent conjugate of the invention wherein the therapeutic agent is a nucleic acid.

Likewise the target population can be an in vitro population of cells such as a tissue or fluid sample or biopsy that has been removed from a patient for diagnostic purposes. The biological sample can be contacted with the ligand-agent conjugate of the invention comprising a diagnostic agent for detection or characterization of the disease state of the patient.

An exogenous population of cells can also include a population of exogenous organisms such as bacteria, mycoplasma, yeast, or fungi, provided the organisms possess a receptor molecule that binds the ligand-agent conjugate. See, e.g., Kumar et al., 1987, *J. Biol. Chem.* 262(15):7171-9. The ligand-agent conjugate binds to the surface of the tumor cells or pathogenic organisms and "labels" or otherwise alters or modifies cell or tissue function; it may or may not be internalized, depending on the intended application.

EXAMPLES

The following examples are illustrative of certain embodiments of the invention. The examples, methods, and conditions presented therein are not to be construed as limiting the scope nor the spirit of the invention.

Example I

Targeting the Tumor-Associated Folate Receptor with a $^{111}In$-DTPA Conjugate of Pteroic Acid Objective. The present study was undertaken to evaluate the structural requirements for folate-receptor-targeting with low-molecular-weight radiometal chelates, specifically examining the role of the amino acid fragment of folic acid (pteroyl-glutamic acid) in mediating folate-receptor affinity.

Methods. The amide-linked conjugate pteroyl-$NHCH_2CH_2OCH_2CH_2OCH_2CH_2NH$-DTPA (CYK4-013), which lacks an amino acid in the linker region, was prepared by a three-step procedure from pteroic acid, 2,2'-(ethylenedioxy)-bis(ethylamine), and t-Bu-protected DTPA.

CKY 4-013

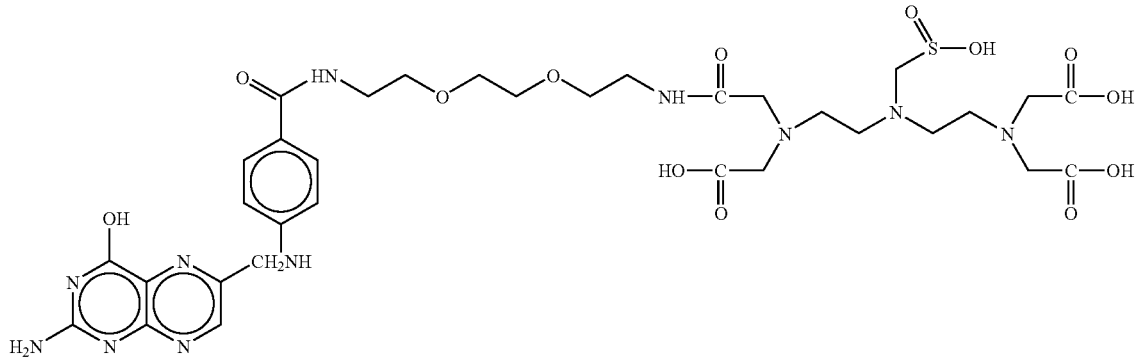

Figure 2:
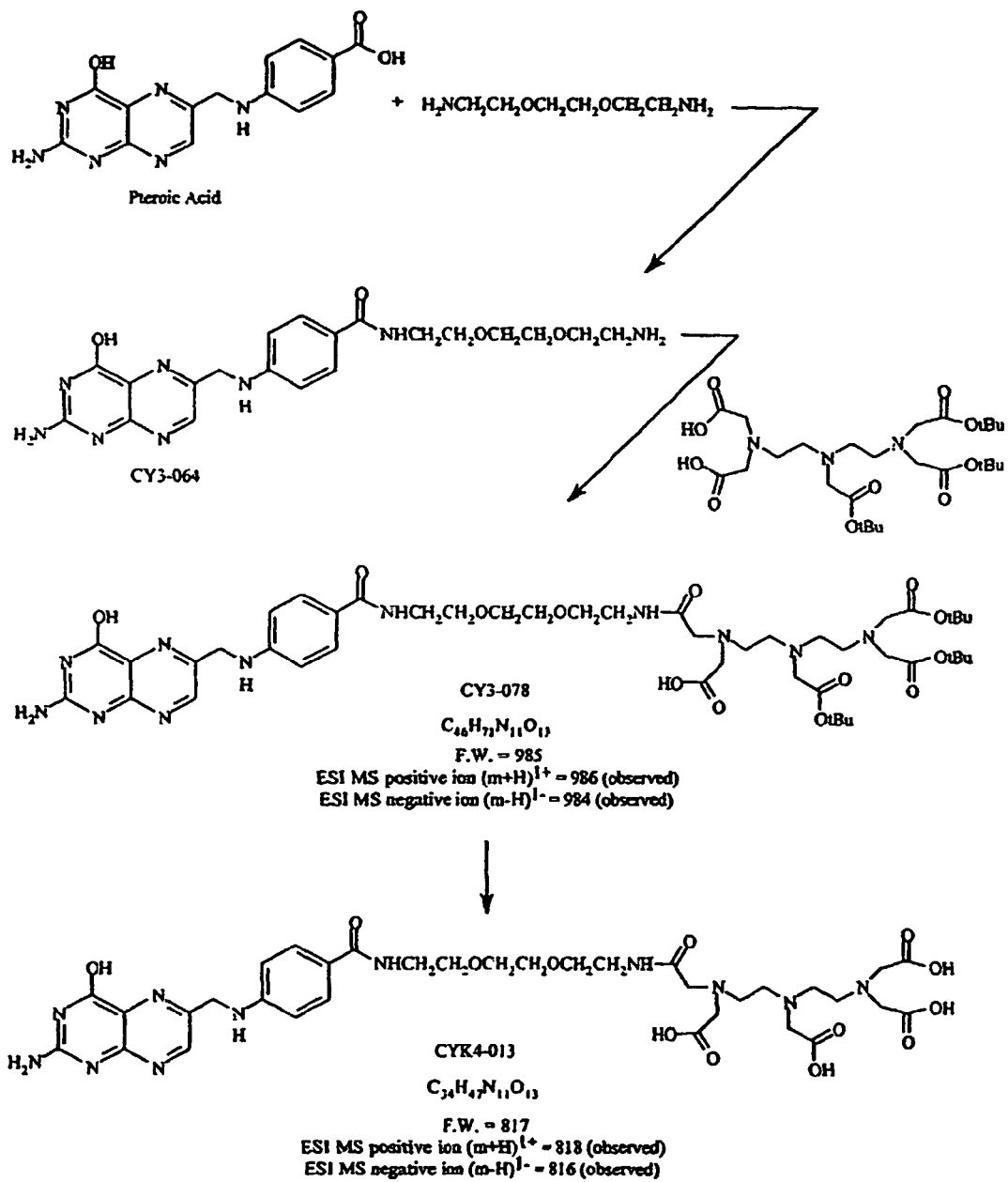
FIG. 2 is a schematic representation of the synthesis of a pteroic acid conjugate, CYK4-013.

This conjugate (CYK4-013) was prepared as outlined in FIG. 2. CY3-064 was obtained from pteroic acid (0.025 g; 0.080 mmol) and a large excess of 2,2'-(ethylenedioxy)-bis (ethylamine) (0.237 g; 1.6 mmol) using the coupling reagents. Benzotriazole-1-yl-oxy-tris(pyrrolidino)phosphonium hexafluorophosphate (PyBOP) (0.125 g; 0.24 mmol), N-hydroxybenzotriazole (HOBt) (0.037 g; 0.24 mmol), and N-methylmorpholine (Nmm) (0.049 g; 0.48 mmol) in dry dimethylsulfoxide (DMSO) (0.8 mL) at room temperature for 22 hours under nitrogen. The excess reagent and solvent DMSO were removed under vacuum and the resulting brown residue triturated with diethylether, methanol, and water to produce 20 mg of CY3-064 as a yellow solid (57% estimated yield).

This yellow solid was then coupled with t-butyl-protected DTPA (synthesized as described by S. A. Chilefu, et al., *J. Org. Chem.*, 2000,65:1562-1565) using the same coupling reagents (0.012 g CY3-064; 0.071 g t-Bu-DTPA, 0.127 mmol; 0.0848 g PyBOP, 0.16 mmol; 0.0249 g HOBt, 0.16 mmol; 0.0247 g Nmm, 0.24 mmol; 0.6 mL dry DMSO). During coupling, the solubility of CY3-064 was very poor in the DMSO solvent, and not improved by addition of more Nmm. 1,3,4,6,7,8-hexahydro-1-methyl-2H-pyrimido[1,2-a]-pyrimidine (MTBD) (0.0083 g; 0.0542 mmol) was added after stirring overnight at room temperature, but the solubility remained poor. After again stirring overnight, the DMSO and excess reagents were removed under high vacuum overnight.

The resulting brown residue was triturated first with diethylether and then with methanol. The methanol suspension was centrifuged to produce crude CY3-078 as a yellow solid. This yellow solid was purified using semi-preparative HPLC (2×) on a C18 column (10×250 mm) to produce pure CY3-078. (HPLC solvent A=5% $CH_3CN$ in 0.1% aqueous TFA; solvent B=10% water in 0.1% TFA in $CH_3CN$. Linear gradients established as: 5% B at time=zero ramping to 70% B at 30 minutes, then ramping to 100% B at 32 minutes, and remaining 100% B to 40 minutes. Flow rate=2.35 mL/min). The peak with retention time of 30.5 minutes was collected. The purified CY3-078 was treated with 70% TFA/$CH_2Cl_2$ at 0° C. for 30 minutes, and stirred at room temperature for 5 hours, to remove the three t-Bu protecting groups. The resulting CYK4-013 product (6 mg) was isolated by trituration with diethylether. Both CY3-078 and CYK4-013 exhibit the expected parent ion peaks in their positive and negative ion electrospray mass spectra. In particular, purified CYK4-013 exhibited the expected parent ion peaks in its positive and negative ion electrospray mass spectra (m/e=818 and 816, respectively).

The $^{111}$In complex of CYK4-013 was prepared from $^{111}$In-chloride (1.2 mCi; 44 MBq) and purified by reversed-phase HPLC. Specifically, the $^{111}$In complex of CYK4-013 was prepared from $^{111}$In-chloride via ligand exchange in acetate buffer. Briefly, 1.2 mCi no-carrier-added $^{111}$In-chloride (Mallinckrodt, Inc., St. Louis) in 0.05 mL 0.05 N HCl was transferred to a small tube and 0.05 mL 0.1N ammonium acetate (pH 5.5), followed by 0.02 mL 0.5N ammonium acetate (pH 7.4) was added, producing a solution with pH 7. The CYK4-013 ligand was weighed out and diluted in water, pH adjusted with 1N NaOH to pH 9-10. 10 µL of this ligand solution containing 95 µg CYK4-013 was added to the $^{111}$In-acetate solution (120 µL) and mixed. The solution was protected from light and kept at room temperature.

The radiochemical purity of the resulting crude $^{111}$In-CYK4-013 was evaluated by radio-HPLC using a 4.6×250 mm Dynamax C18 column (Varian/Rainin) eluted with an aqueous $NH_4OAc$:acetonitrile gradient. HPLC conditions: Solvent A=56 mM $NH_4OAc$ in water; Solvent B=$CH_3CN$. Flow rate=1 mL/min on 4.6×250 mm C18 reverse-phase column. Linear gradient conditions: 5% B at zero minutes, ramping to 25% B at 25 minutes, then ramping to 60% B at 27 minutes and 100% B at 30 minutes).

The major radioactive HPLC peak, eluting with a retention time of 14.1 minutes, was collected. HPLC analysis of this isolated peak showed it to remain stable for at least 7 days at room temperature. HPLC conditions: Solvent A=56 mM $NH_4OAc$ in water; Solvent B=$CH_3CN$. Flow rate=1 mL/min on 4.6×250 mm C18 reverse-phase column. Linear gradient conditions: 5% B at zero minutes, ramping to 25% B at 25 minutes, then ramping to 60% B at 27 minutes and 100% B at 30 minutes.

Radio-TLC of the HPLC-purified $^{111}$In-CYK4-013 was performed using a C18 plate eluted with 25% $NH_4OAc$; 75% acetonitrile. The results confirm the absence of $^{111}$In-species that irreversibly adsorb to C18 (i.e., there is no $^{111}$In remaining at origin)

The HPLC-purified $^{111}$In-CYK4-013 was removed from the HPLC solvents by solid-phase extraction. A C18 Sep-Pak Light solid phase extraction cartridge (Millipore, Inc.) was conditioned by washing with ethanol followed by water. The $^{111}$In-CYK4-013 was loaded onto the C18 Sep-Pak after dilution with water to 5% acetonitrile, the Sep-Pak was washed with 3 mL water, and the $^{111}$In-CYK4-013 product was recovered by fractional elution with ethanol. The resulting ethanol solution of $^{111}$In-CYK4-013 was evaporated to dryness under a stream of $N_2$ at room temperature, and the $^{111}$In-CYK4-013 was reconstituted in saline for use in a biodistribution study in mice.

Our primary animal model for evaluation of the biodistribution and pharmacokinetics of folate-receptor-targeted radiopharmaceuticals has been athymic mice bearing subcutaneously implanted folate-receptor-positive human KB cell tumors. Because normal rodent chow contains a high concentration of folic acid (6 mg/kg chow), the mice used in these receptor targeting studies were maintained on folate-free diet for 3 weeks to achieve serum folate concentrations close to the 4-6 μg/L (9-14 nM) range of normal human serum. After 3 weeks on folate-free diet, mouse serum folate levels drop to 25±7 nM from the initial 720±260 nM serum folate level when the animals are fed normal rodent chow. This dietary intervention is believed to be a reasonable manipulation of the animal model, since the mice would have serum folate levels only slightly higher than the folate concentration of normal human serum. Thus, in these mouse biodistribution studies the radiotracer is competing for tumor folate receptors with physiologically relevant concentrations of endogenous unlabeled serum folate.

Thus, to demonstrate the ability of such conjugates to selectively localize in folate-receptor-positive tissues, the biodistribution of $^{111}$In-CYK4-013 was determined following intravenous administration to athymic mice with subcutaneous folate-receptor-positive human KB cell tumor xenografts. The resulting data are presented in Tables 1 and 2. The $^{111}$In-CYK4-013 agent is found to selectively localize in the folate-receptor-positive tumors (5.4±0.8 and 5.5±1.1 percent of the injected $^{111}$In dose per gram of tumor at 1 hour and 4 hours post-injection, respectively) and to exhibit prolonged tumor retention of the radiolabel (3.6±0.6 percent of the injected $^{111}$In dose per gram of tumor still remaining at 24 hours post-injection). The tumor localization of the $^{111}$In-radiolabel clearly appears to be mediated by the cellular folate receptor, since the tumor uptake of radiotracer drops precipitously (0.12±0.07 percent of the injected $^{111}$In dose per gram at 4 hours) when $^{111}$In-CYK4-013 is co-injected with an excess of folic acid, which will compete for folate receptor sites. Urinary excretion appears to be the primary whole-body clearance pathway for the $^{111}$In-CYK4-013. The substantial retention of $^{111}$In in the kidneys is fully consistent with the binding of $^{111}$In-CYK4-013 to tissue folate receptors, since the renal proximal tubule is a known normal tissue site of folate receptor expression. This interpretation is supported by the expected and observed marked reduction in renal $^{111}$In when $^{111}$In-CYK4-013 is co-administered with excess folic acid. The behavior of the $^{111}$In-CYK4-013 radiopharmaceutical in this animal model (Table 2) is very similar to that observed for $^{111}$In-DTPA-Folate (Table 3).

Results. Biodistribution of $^{111}$In-CYK4-013 is shown in Tables 1-3. Similar to $^{111}$In-DTPA-Folate, $^{111}$In-CYK4-013 selectively localized in the folate-receptor-positive tumor xenografts, and afforded prolonged tumor retention of [111]In (5.4±0.8; 5.5±1.1; and 3.6±0.6% ID/g at 1 hour, 4 hours, and 24 hours, respectively) (Table 2). The tumor localization of the $^{111}$In-radiolabel appears to be mediated by the cellular folate receptor, since the tumor uptake dropped precipitously (0.12±0.07% ID/g at 4 hours) when $^{111}$In-CYK4-013 was co-injected with an excess of folic acid (Table 2). Blockable binding was also observed in the kidneys, where the folate receptor occurs in the proximal tubules.

TABLE 1

Biodistribution of $^{111}$In-CYK4-013 in KB Tumor-Bearing Athymic Mice at Various Times Following Intravenous Administration

| | Percentage of Injected [111]In Dose Per Organ (Tissue) | | | |
|---|---|---|---|---|
| | 1 Hour | 4 Hours | 4 Hours-Blocked** | 24 Hours |
| Tumormass (g): | 0.15 ± 0.10 | 0.080 ± 0.031 | 0.077 ± 0.010 | 0.104 ± 0.097 |
| Animalmass (g): | 29.5 ± 1.2 | 28.6 ± 1.6 | 28.2 ± 1.1 | 28.6 ± 0.8 |
| Animal Quantity & Gender: | 3M | 4M | 4M | 4M |
| Blood: | 0.29 ± 0.003 | 0.078 ± 0.010 | 0.025 ± 0.015 | 0.055 ± 0.0002 |
| Heart: | 0.51 ± 0.09 | 0.41 ± 0.08 | 0.0023 ± 0.0016 | 0.18 ± 0.06 |
| Lungs: | 0.69 ± 0.06 | 0.60 ± 0.01 | 0.0082 ± 0.0051 | 0.34 ± 0.03 |
| Liver & Gall Bladder: | 6.8 ± 1.3 | 3.0 ± 1.0 | 0.074 ± 0.044 | 1.7 ± 0.9 |
| Spleen: | 0.063 ± 0.016 | 0.049 ± 0.012 | 0.0049 ± 0.0029 | 0.055 ± 0.017 |
| Kidney (one): | 15.3 ± 1.2 | 20.2 ± 1.6 | 0.23 ± 0.15 | 26.8 ± 2.7 |
| Stomach, Intestines & Contents: | 5.8 ± 0.5 | 5.4 ± 0.8 | 4.6 ± 2.8 | 3.3 ± 0.6 |
| Muscle: | 43.6 ± 4.1 | 33 ± 9 | 1.0 ± 0.7 | 23.1 ± 7.0 |
| Tumor: | 0.78 ± 0.47 | 0.46 ± 0.26 | 0.0094 ± 0.0061 | 0.42 ± 0.4 |

*Athymic mice (NuNu strain) with subcutaneous tumors. Born Sep. 11, 2000. Arrived Oct. 10, 2000. Initiated folate free diet Oct. 10, 2000. Implanted on Oct. 20, 2000; 0.25 × 10⁶ KB cells (passage 9) per animal subcutaneous in intrascapular region. Study date: Nov. 2, 2000. Values shown represent the mean ± standard deviation. Blood was assumed to account for 5.5% of total body mass. Muscle was assumed to account for 42% of the total body mass.
**Folate receptors blocked by co-injection of folic acid dihydrate at a dose of 4.1 ± 0.4 mg/kg.

TABLE 2

Biodistribution of $^{111}$In-CYK4-013 in KB Tumor-Bearing Athymic Mice at Various Times Following Intravenous Administration

| | Percentage of Injected [111]In Dose Per Gram (Tissue Wet Mass) | | | |
|---|---|---|---|---|
| | 1 Hour | 4 Hours | 4 Hours-Blocked** | 24 Hours |
| Tumormass (g): | 0.15 ± 0.10 | 0.080 ± 0.031 | 0.077 ± 0.010 | 0.104 ± 0.097 |
| Animalmass (g): | 29.5 ± 1.2 | 28.6 ± 1.6 | 28.2 ± 1.1 | 28.6 ± 0.8 |
| Animal Quantity & Gender: | 3M | 4M | 4M | 4M |

TABLE 2-continued

Biodistribution of $^{111}$In-CYK4-013 in KB Tumor-Bearing Athymic Mice at Various Times Following Intravenous Administration

| | Percentage of Injected $^{111}$In Dose Per Gram (Tissue Wet Mass) | | | |
|---|---|---|---|---|
| | 1 Hour | 4 Hours | 4 Hours-Blocked** | 24 Hours |
| Blood: | 0.18 ± 0.01 | 0.050 ± 0.009 | 0.016 ± 0.010 | 0.035 ± 0.002 |
| Heart: | 3.5 ± 0.4 | 2.9 ± 0.9 | 0.015 ± 0.010 | 1.2 ± 0.5 |
| Lungs: | 1.5 ± 0.2 | 1.4 ± 0.3 | 0.041 ± 0.027 | 0.72 ± 0.21 |
| Liver & Gall Bladder: | 4.3 ± 0.7 | 1.9 ± 0.6 | 0.051 ± 0.029 | 1.2 ± 0.6 |
| Spleen: | 0.31 ± 0.09 | 0.29 ± 0.07 | 0.028 ± 0.017 | 0.27 ± 0.08 |
| Kidney (one): | 61 ± 5 | 81 ± 7 | 0.90 ± 0.59 | 105 ± 7 |
| Stomach, Intestines & Contents: | 1.7 ± 0.2 | 1.5 ± 0.9 | 1.7 ± 1.1 | 1.2 ± 0.2 |
| Muscle: | 3.5 ± 0.5 | 2.8 ± 0.8 | 0.080 ± 0.057 | 1.9 ± 0.6 |
| Tumor: | 5.4 ± 0.8 | 5.6 ± 1.1 | 0.12 ± 0.07 | 3.6 ± 0.6 |
| Tumor/blood | 30 ± 5 | 111 ± 11 | 7.5 ± 2.4 | 105 ± 20 |
| Tumor/kidney | 0.088 ± 0.013 | 0.069 ± 0.013 | 0.12 ± 0.03 | 0.035 ± 0.008 |
| Tumor/liver | 1.3 ± 0.4 | 3.0 ± 0.5 | 2.2 ± 0.6 | 3.7 ± 1.4 |
| Tumor/muscle | 1.6 ± 0.4 | 2.1 ± 0.2 | 1.5 ± 0.7 | 2.0 ± 0.6 |

*Athymic mice (NuNu strain) with subcutaneous tumors. Values shown represent the mean ± standard deviation.
**Folate receptors blocked by co-injection of folic acid dihydrate at a dose of 4.1 ± 0.4 mg/kg.

TABLE 3

Biodistribution of $^{111}$In-DTPA-Folate in Athymic Mice with Subcutaneous KB Cell Tumor Xenografts

| | Percentage of Injected $^{111}$In Dose Per Gram (mean ± s.d.; n = 4) | | |
|---|---|---|---|
| | 1 Hour Post Injection | 4 Hours Post Injection | 4 Hours Post Injection BLOCKED |
| Tumormass (g): | 0.138 ± 0.051 | 0.202 ± 0.083 | 0.193 ± 0.078 |
| Animalmass (g): | 24 ± 2 | 25 ± 1 | 24 ± 1 |
| Folic Acid Dose (μg/kg): | 0 | 0 | 495 ± 79 |
| Blood: | 0.14 ± 0.03 | 0.064 ± 0.007 | 0.029 ± 0.011 |
| Heart: | 2.3 ± 0.4 | 2.0 ± 0.3 | 0.022 ± 0.010 |
| Lungs: | 1.3 ± 0.1 | 1.1 ± 0.3 | 0.065 ± 0.021 |
| Liver & Gall Bladder: | 4.0 ± 1.5 | 2.2 ± 0.4 | 0.12 ± 0.03 |
| Spleen: | 0.36 ± 0.03 | 0.35 ± 0.11 | 0.060 ± 0.021 |
| Kidney: | 90 ± 9 | 85 ± 12 | 2.3 ± 1.0* |
| Stomach, Intestines & Contents: | 1.0 ± 0.2 | 1.0 ± 0.2 | 0.49 ± 0.20 |
| Muscle: | 3.5 ± 0.8 | 2.9 ± 0.7 | 0.023 ± 0.013 |
| Tumor: | 5.3 ± 0.4 | 6.8 ± 1.2 | 0.16 ± 0.07 |
| Tumor/blood | 38 ± 7 | 106 ± 15 | 5.5 ± 0.8 |
| Tumor/kidney | 0.060 ± 0.011 | 0.080 ± 0.012 | 0.050 ± 0.023 |
| Tumor/liver | 1.5 ± 0.5 | 3.3 ± 1.1 | 1.4 ± 0.4 |
| Tumor/muscle | 1.6 ± 0.3 | 2.5 ± 0.9 | 8.4 ± 3.8 |

*n = 3 (While 4 animals were studied, one gave an unusually high value for the kidney uptake with no apparent underlying cause for the disparity with the other animals in this group. If that anomalous value is included, this result becomes 5.0 ± 5.5% ID/g, n = 4).

Conclusion. Tumor-selective drug targeting via the folate receptor remains feasible with pteroic acid conjugates lacking amino acid fragments, such as the glutamic acid moiety of folic acid.

Example II

Synthesis of a DOTA Conjugate of Pteroic Acid

Figure 3:
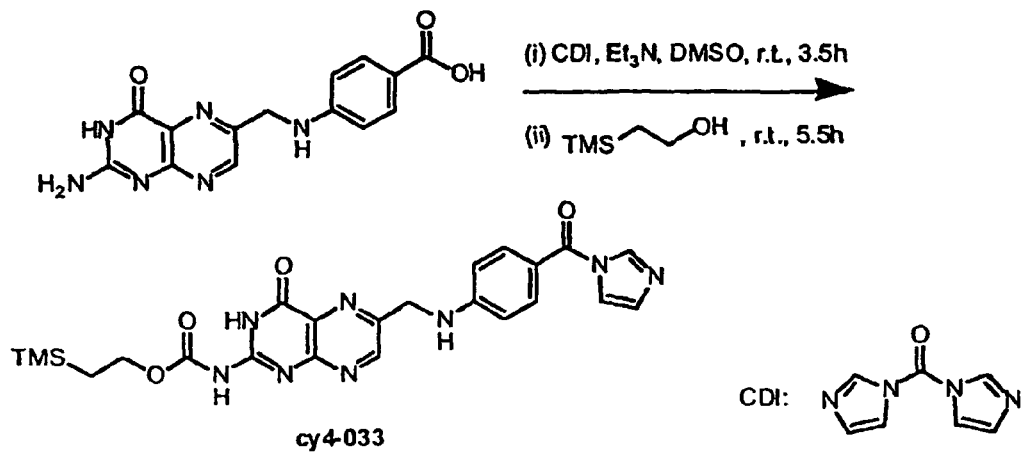
FIG. 3 is a schematic representation of the synthesis of pteroic acid conjugate linked to the tetraazamacrocyclic DOTA chelating ligand (CY4-036).
Figure 3:
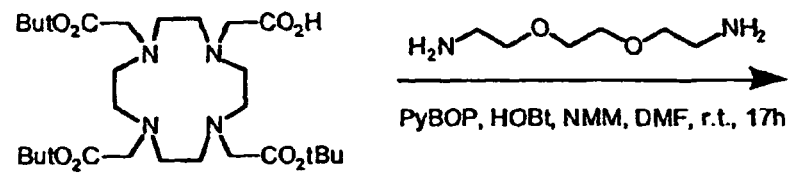
Figure 3:
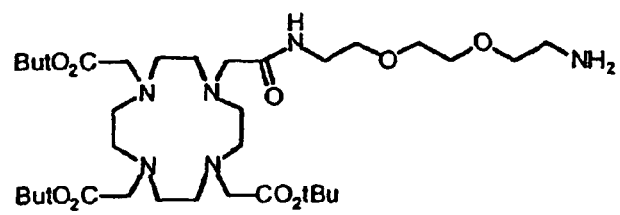
Figure 3:
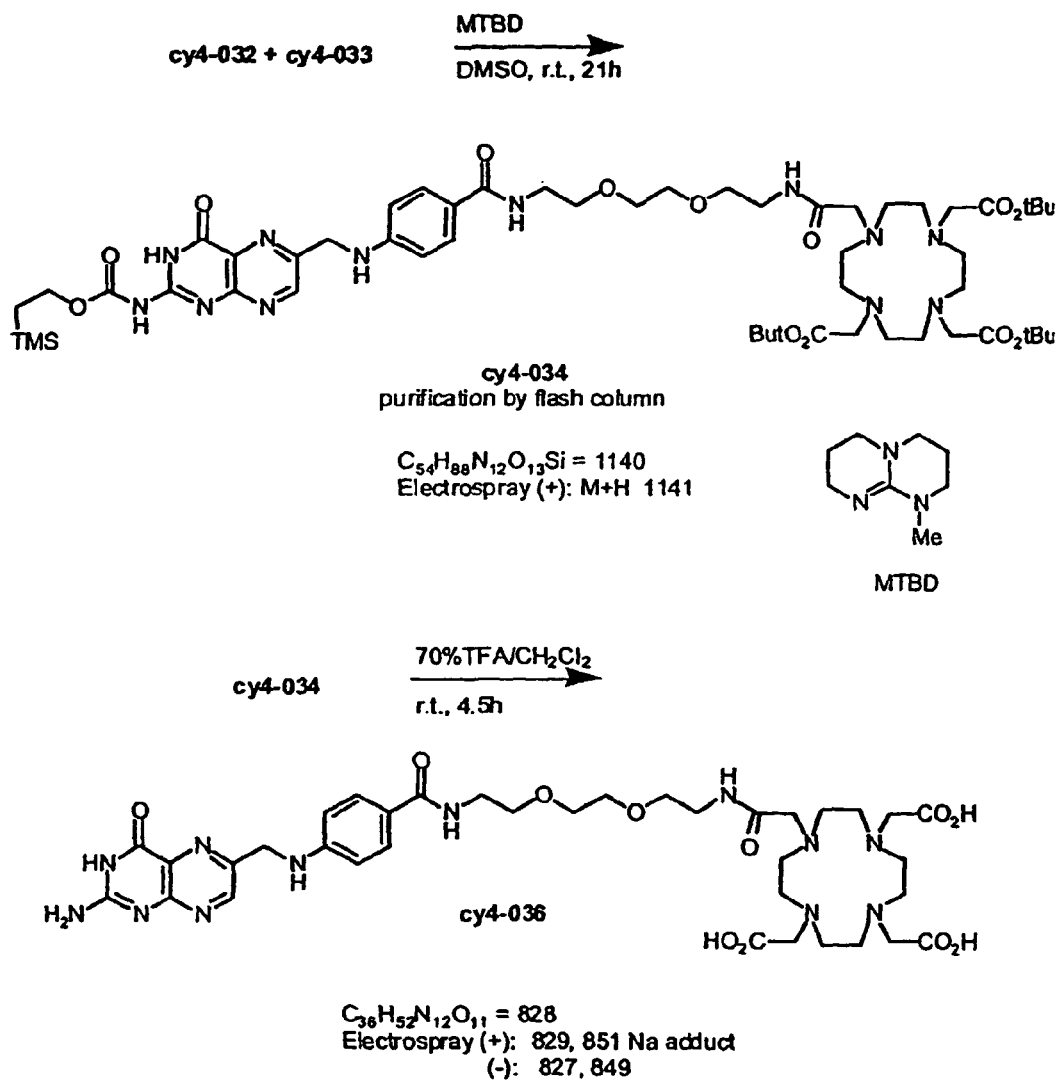

A pteroic acid conjugate linked to the tetraazamacrocyclic DOTA chelating ligand was prepared for radiolabeling with radiometals such as $^{64}$Cu$^{2+}$ and $^{111}$In$^{3+}$. This conjugate (CY4-036) was prepared as shown in FIG. 3. The starting material for the synthesis was pteroic acid. Due to the poor solubility of pteroic acid in organic solvent, pteroic acid was protected with 2-(trimethylsilyl)ethanol to produce intermediate CY4-033 using literature procedure (M. Nomura, et al., *J. Org. Chem.*, 2000, 65, 5016-5021) to increase its solubility in organic solvent before coupling to the DOTA derivative.

DOTA was coupled to 2,2'-(ethylenedioxy)bis(ethyleneamine) using PyBOP, HOBt, and NMM as coupling reagents in DMF to produce CY4-032. Protected form of pteroyl-linker-DOTA (CY4-034) was obtained through the coupling of CY4-032 and CY4-033 in DMSO using MTBD as a base, and then purified via flash chromatography eluted with gradient MeOH/CHCl$_3$.

All the protecting groups (three t-butyl groups on carboxylic acids and one 2-(trimethylsilyl)ethyloxycarbonyl on nitrogen) were removed by the treatment with 70% TFA/CH2Cl2 to produce CY4-036.

Synthesis of CY4-032. To a solution of DOTA-tri-t-butyl ester (0.050 g, 0.087 mmol), PyBOP (0.136 g, 0.261 mmol), and HOBt (0.052 g, 0.339 mmol) in DMF (0.9 mL) was added NMM (0.035 g, 0.348 mmol) under N$_2$. The clear solution was stirred at room temperature (i.e., about 25° C.) for 10 minutes followed by the addition of 2,2'-(ethylenedioxy)bis (ethyleneamine) (0.065 g, 0.436 mmol) under N$_2$. After stirring at room temperature for 17 h, the solution was concentrated under high vacuum to remove DMF and excess reagents. The oily residue was triturated with Et$_2$O (3×5 mL). After the removal of Et$_2$O, EtOAc (3 mL) was added followed by 2 mL of water. After stirring for 2 minutes, the EtOAc was separated from aqueous layer and then more EtOAc (3 mL) was added for the extraction of product. The extraction was repeated one more time. All three EtOAc layers were combined, concentrated, and then dried under high vacuum to produce 0.153 g of oily crude product. $C_{34}H_{66}N_6O_9=702$; Electrospray (+): M+H 703. This crude material was used for the next coupling step without further purification.

Synthesis of CY4-033. To a suspension of carbonyl diimidazole (CDI) (0.069 g, 0.425 mmol) and pteroic acid (0.028 g, 0.090 mmol) in DMSO (0.8 mL) was added triethylamine (0.032 g, 0.32 mmol) under N$_2$. After stirring at room temperature for 3.5 hours, 2-(trimethylsilyl)ethanol (0.076 g, 0.64 mmol) was added and stirred at room temperature for 5.5 hours. The reaction mixture was concentrated under high vacuum overnight to remove DMSO and excess reagents. Yellow residue was produced and triturated with Et$_2$O. A yellow solid (0.067 g) was produced as crude product. This crude material was used for next reaction without further purification.

Synthesis of CY4-034. To a solution of CY4-032 (0.153 g) and CY4-033 (0.067 g) in DMSO (0.8 mL) was added MTBD (0.041 g, 0.27 mmol) under $N_2$. After stirring at room temperature for 21 hour, the reaction mixture was dried under high vacuum to remove DMSO and excess reagents to produce 0.157 g of yellow residue. This crude product was purified via flash chromatography eluted with gradient MeOH/ $CHCl_3$ to produce 0.073 g of pure CY4-034.

Synthesis of CY4-036. 70% $TFA/CH_2Cl_2$ (1 mL) was added to the purified CY4-034 (0.018 g) at room temperature. After stirring at room temperature for 4.5 hour, the reaction mixture was concentrated under reduced pressure and dried under high vacuum overnight to produce 19 mg of crude product. All three t-Butyl groups and the 2-(trimethylsilyl) ethyloxycarbonyl protecting group were removed at this step.

$^{64}$Cu-complex of CY4-036. The $^{64}$Cu complex of CY4-036 was prepared from $^{64}$Cu-chloride via ligand exchange in acetate buffer. Briefly, 2.88 mCi of no-carrier-added $^{64}$Cu-chloride (Washington University, St. Louis, Mo.) in 0.005 mL of 0.01 N HCl was transferred to a small test tube and mixed with 0.010 mL of 0.5 M ammonium acetate (pH 7.4). The CY4-036 ligand was weighed out and diluted in water and the pH adjusted with 1 N NaOH to pH 11-12. One μL of this ligand solution containing ~125 μg CY4-036 was added to the $^{64}$Cu-acetate solution and mixed. The pH of the solution was adjusted to pH 8-9 with the addition of 1 μL of 1 N NaOH. The solution was protected from light and incubated at 65° C. for 30 minutes.

The resulting crude $^{64}$Cu-CY4-036 was diluted with water and injected onto radio-HPLC using a 10×250 mm Dynamax C18 column (Varian/Rainin) eluted with an aqueous $NH_4OAc$:acetonitrile gradient. HPLC conditions: Solvent A=56 mM $NH_4OAc$ in water; Solvent B=$CH_3CN$. Flow rate=2.35 mL/min on 10×250 mm C18 reverse-phase column. Linear gradient conditions: 5% B at zero minutes, ramping to 25% B at 25 minutes, then ramping to 60% B at 27 minutes and 100% B at 30 minutes. The major radioactive HPLC peak, eluting with a retention time of 20.9 minutes, was collected. Radio-TLC confirmed the absence of $^{64}$Cu(II)-acetate, which was independently shown to remain at the origin.

HPLC-purified $^{64}$Cu-CY4-036 was removed from the HPLC solvents by solid-phase extraction. A C18 Sep-Pak Light solid phase extraction cartridge (Millipore, Inc.) was conditioned by washing with ethanol followed by water. The HPLC-purified $^{64}$Cu-CY4-036 was loaded onto the C18 Sep-Pak after dilution with water to 5% acetonitrile, the Sep-Pak was washed with 20 mL water, and the $^{64}$Cu-CY4-036 product recovered by fractional elution with ethanol. The resulting ethanol solution of $^{64}$Cu-CY4-036 was evaporated to dryness under a stream of $N_2$ at room temperature, and the $^{64}$Cu-CY4-036 was reconstituted in water. Analytical HPLC confirmed the radiochemical purity, and stability, of the isolated $^{64}$Cu-CY4-036 product. HPLC conditions: Solvent A=53 mM $NH_4OAc$ in water; Solvent B=$CH_3CN$. Flow rate=1 mL/min on 4.6×250 mm C18 reverse-phase analytical column. Linear gradient conditions: 5% B at zero minutes, ramping to 25% B at 25 minutes, then ramping to 60% B at 27 minutes and 100% B at 30 minutes.

Example III

Mandelic Acid Conjugate of Pteroic Acid

Figure 4:
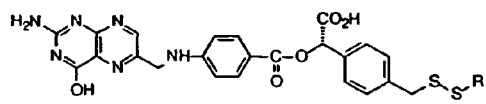
FIG. 4 is a schematic representation of the metabolism of a ligand-agent conjugate of the invention involving bioreduction to release the agent.
Figure 4:
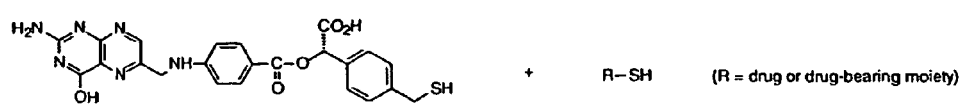
Figure 5:
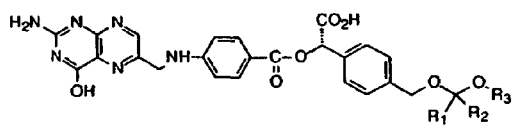
FIG. 5 is a schematic representation of the metabolism of a ligand-agent conjugate of the invention involving acid hydrolysis to release the agent.
Figure 5:
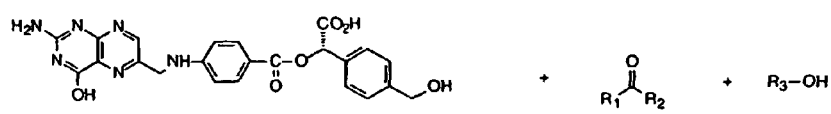

Biodegradation of an ester formed from pteroic acid and a substituted derivative of mandelic acid is shown in FIGS. 4 and 5. FIG. 4 illustrates bioreduction of the conjugate to release the drug or drug-bearing moiety, while FIG. 5 illustrates acid hydrolysis of the conjugate to release the drug or drug-bearing moiety. Evidence from a recent article describing structure-activity relationships of the folate receptor suggests that the proton on the nitrogen which forms part of the amide bond between pteroic acid and glutamic acid is not necessary for high-affinity binding (Westerhoff et al., 1995, *Molecular Pharmacology* 48, 459-471). Accordingly, it is highly anticipated that the mandelate esters depicted in these schemes will bind with high affinity to the folate receptor. An example is shown in Example IV.

Example IV

Synthesis and Activity of (S)-α-carboxybenzoyl pteroate (ACBP) and N-pteroyl-2-amino-2-carboxymethylpyridine (Pte-AP)

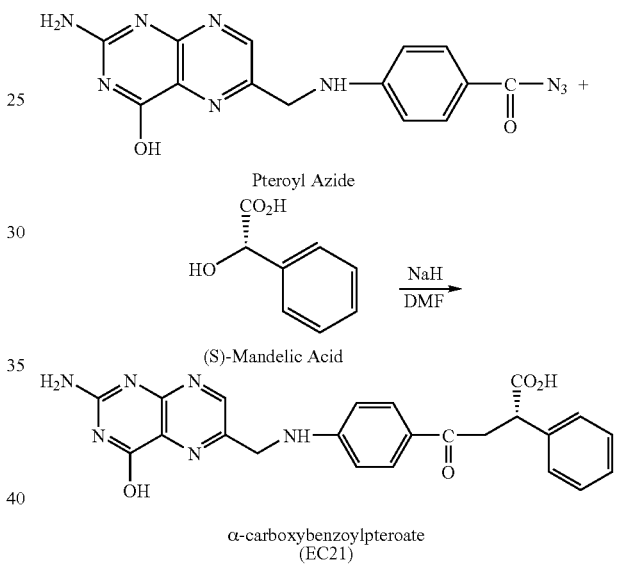

Synthesis of ACBP. (S)-α-carboxybenzoyl pteroate (ACBP) is a mandelate ester (see Example III). A solution of (S)-mandelic acid (28 mg, 0.187 mmol) in 2 mL of anhydrous dimethylformamide was added via syringe to 30 mg of a 60% dispersion of NaH in mineral oil (under argon). After stirring for 10 minutes at room temperature, solid pteroyl azide (64 mg, 0.187 mmol) was added and the reaction was stirred for an additional 2 hours. The reaction was quenched with a solution of 50 mg $NH_4Cl$ in 60 mL of deionized water. The resulting solution was washed with hexanes (to remove the mineral oil) and then diethylether. The aqueous solution was sparged with argon while the flask was immerged in warm water to evaporate the residual diethylether. The solution was brought to pH 2.2 by drop-wise addition of 1 N HCl, whereupon the product precipitated as a yellow-orange finely-divided solid. The solid was isolated by centrifugation and washed twice with deionized water. The material was dissolved in 6 mL of deionized water containing $NH_4HCO_3$ (16 mg, 0.2 mmol). The resulting solution was filtered and then purified by HPLC: Novapak 19×300 mm prep column, gradient 0-40% B in 35 minutes; A=10 mM $NH_4HCO_3$, B=$CH_3CN$. $R_t$ about 16.5 minutes.

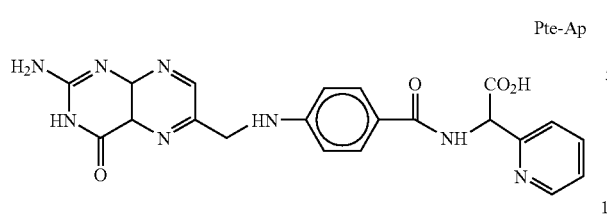

Pte-Ap

Relative binding affinity. To determine how well these compounds competes with 3H-folic acid for binding to the folate receptor (FR)-positive cell line, KB (available from the American Type Culture Collection, ATCC #CCL-17), a binding assay was conducted. The relative affinity of various folate derivatives was determined according to the method described by Westerhoff et al. (Mol. Pharm., 1995, 48:459-471) with slight modification. Briefly, folate receptor-positive KB cells were gently trypsinized in 0.25% trypsin in phosphate-buffered saline (PBS) at room temperature for 3 minutes and then diluted in folate-free RPMI 1640 media (FFRPMI) (Gibco) supplemented with 10% heat-inactivated fetal calf serum. Following a 5 minute 800×g spin and one PBS wash, the final cell pellet was suspended in FFRPMI (no serum). Cells were incubated for 15 minutes on ice with 100 nM of $^3$H-folic acid in the absence and presence of increasing concentrations of pteroate-containing test articles. Samples were centrifuged at 10,000×g for 5 minutes, cell pellets were suspended in buffer, transferred to individual vials containing 5 mL of scintillation cocktail, and then counted for radioactivity. Negative control tubes contained only the $^3$H-folic acid in FFRPMI (no competitor). Positive control tubes contained a final concentration of 1 mM folic acid, and counts per minute (CPM) measured in these samples (representing non-specific binding of label) were subtracted from all samples. Relative affinities were defined as the inverse molar ratio of compound required to displace 50% of $^3$H-folic acid bound to folate receptor on KB cells, and the relative affinity of folic acid for the folate receptor was set to 1.

Figure 6:
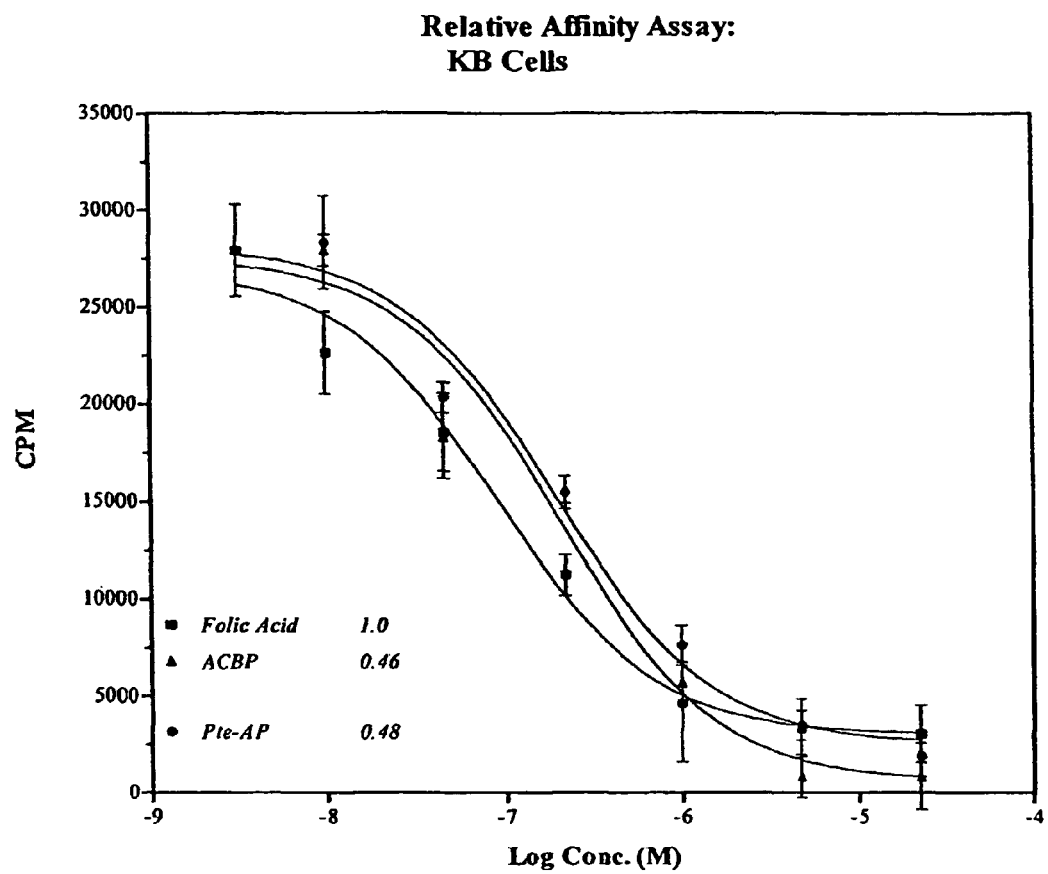
FIG. 6 depicts the binding activity of (S)-α-carboxybenzoyl pteroate (ACBP) and N-pteroyl-2-amino-2-carboxymethylpyridine (Pte-AP).

Results. The result of the binding assay are shown in FIG. 6. The ester ACBP showed a relative binding activity of 0.46 compared to folic acid, and an EC50 of 204 nM compared to 93.4 nM for folic acid. The folate analog containing an amide bond, Pte-AP, showed a relative binding activity of 0.48 compared to folic acid, and an EC50 of 193 nM compared to 93.4 nM for folic acid.

Example V

Pteroyl Hydrazide and Derivative

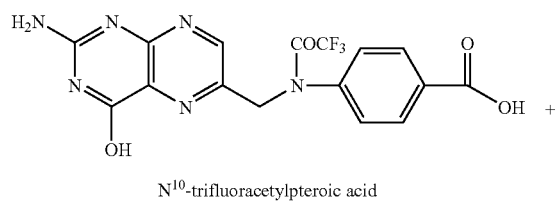

$N^{10}$-trifluoroacetylpteroic acid

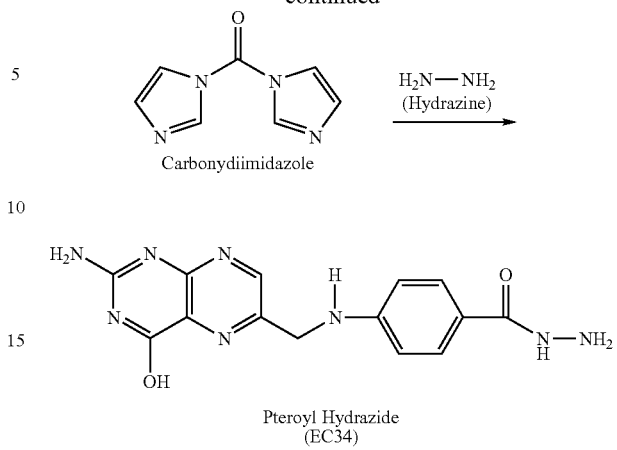

Pteroyl Hydrazide (EC34)

Synthesis of pteroyl hydrazide (Pte-hydrazide). $N^{10}$-trifluoroacetylpteroic acid (40 mg, 0.098 mmol) and carbonyldiimidazole (25 mg, 0.154 mmol) were dissolved in 2 mL of dimethylformamide and stirred under argon at room temperature for 40 minutes. Hydrazine (40 µL; 1.28 mmol) was added to the reaction vessel via syringe. A precipitate immediately formed. Following 15 minutes of stirring, several mL of deionized water were added, and the product was isolated by centrifugation. No further purification was needed.

Figure 7:
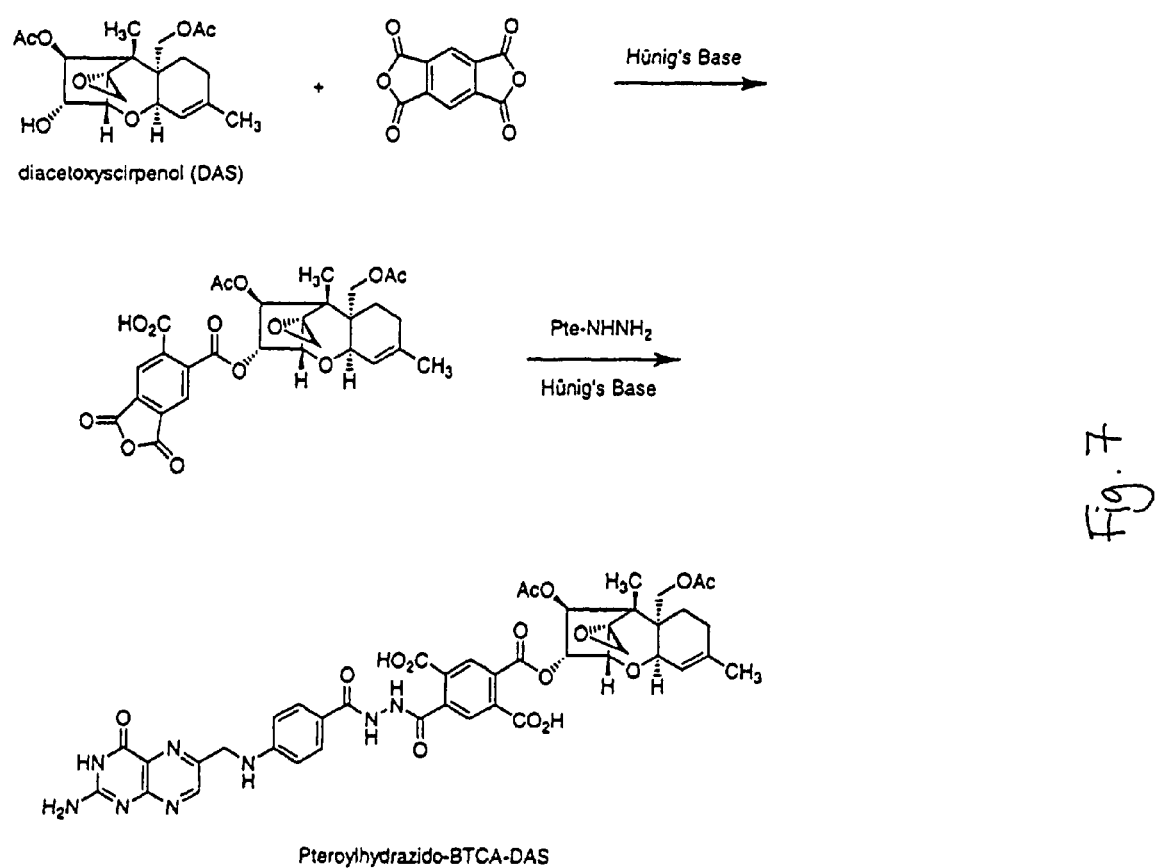
FIG. 7 is a schematic representation of the synthesis of pteroylhydrazido-benzenetetracarboxylic acid-diacetoxyscirpenol (Pte-hydrazideo-BTCA-DAS).

Synthesis of pteroylhydrazido-BTCA-DAS. The synthesis of pteroylhydrazido BTCA-DAS is shown in FIG. 7. To a solution of diacetoxyscirpenol (DAS) (50 mg, 0.137 mmol) in 2.5 mL CH3CN was added 30 mg (0.137 mmol) benzenetetracarboxylic dianhydride followed by 24 µL Hünig's base (17.7 mg, 0.137 mmol, also known as DIPEA, diisopropylethylamine). The reaction mixture was stirred 1.5 hour under argon at room temperature. Some DAS remained, so an additional 6 mg anhydride was added and stirring was continued an additional 1 hour and 10 minutes. Pteroyl hydrazide (59 mg, 0.17 mmol) in 2.5 mL anhydrous dimethylsulfoxide (DMSO) was added, followed by an additional 24 µL (0.137 mmol) of Hünig's base. The reaction was stirred for 1 hour and 10 minutes and precipitated by the addition of ethanol.

Binding activity. The binding activity of pteroyl hydrazide and pteroylhydrazido-BTCA-DAS was determined using the assay described in Example IV.

Figure 8:
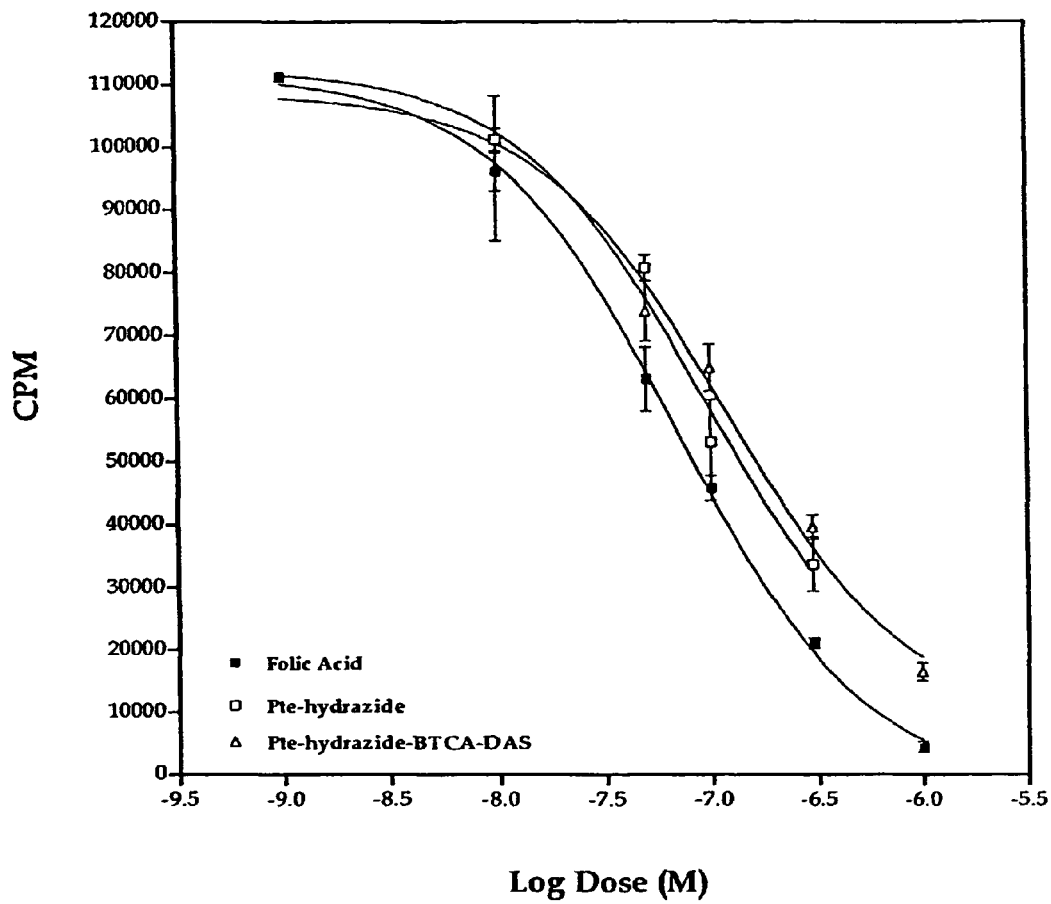
FIG. 8 depicts the binding activity of pteroyl hydrazide (Pte-hydrazide) and Pte-hydrazido-BTCA-DAS.

Results. The results of the binding assay are shown in FIG. 8. Pteroyl hydrazide showed a relative binding activity of 0.74 compared to folic acid, and an EC50 of 94 nM compared to 70 nM for folic acid. Pteroylhydrazido-BTCA-DAS showed a relative binding activity of 0.60 compared to folic acid, and an EC50 of 116 nM compared to 70 nM for folic acid.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

The invention claimed is:

1. A ligand-agent conjugate having the formula

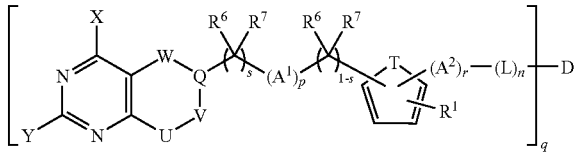

wherein X and Y are each independently selected from the group consisting of halo, $R^2$, $OR^2$, $SR^3$, and $NR^4R^5$;

U, V, and W represent divalent moieties wherein U and W are —N= or —N($R^{4"}$)— and V is —($R^{6'}$)C= or —($R^{6'}$)C—($R^{7'}$)—;

Q is selected from the group consisting of C and CH;

T is selected from the group consisting of S, O, N and —C=C— such that the ring structure of which T is a member is aromatic;

$A^1$ and $A^2$ are each independently selected from the group consisting of —C(S)—, —C(Z)O—, —OC(Z)—, —N($R^{4"}$)—, —C(Z)—N($R^{4"}$)—, —N($R^{4"}$)—C(Z), —O—C(Z)—N($R^{4"}$)—, —N($R^{4"}$)—C(Z)—O—, —N($R^{4"}$)—C(Z)—N($R^{5"}$)—, —O—, —S—, —S(O)—, —S(O)$_2$—, —N($R^{4"}$)S(O)$_2$—, —C($R^{6"}$)($R^{7"}$)—, —N(C≡CH)—, —N(CH$_2$—C≡CH)—, —$C_1$-$C_{12}$ alkyl and $C_1$-$C_{12}$ alkoxy; where Z is oxygen or sulfur provided that $A^2$ does not represent —C(O)NH—;

$R^1$ is selected from the group consisting of hydrogen, halo, $C_1$-$C_{12}$ alkyl, and $C_1$-$C_{12}$ alkoxy;

$R^2$, $R^3$, $R^4$, $R^{4'}$, $R^{4"}$, $R^5$, $R^{5"}$, $R^6$ and $R^7$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or $R^6$ and $R^7$ are taken together to form O=;

$R^{6'}$ and $R^{7'}$ are each independently selected from the group consisting of hydrogen, halo, $C_1$-$C_{12}$ alkyl, and $C_1$-$C_{12}$ alkoxy; or $R^6$ and $R^7$ are taken together to form O=;

L is a divalent linker;

n, p, r and s are each independently either 0 or 1 provided when n=1, then r=1;

q is an integer ≧1;

D is diagnostic agent or a therapeutic agent; and provided that the linker L does not include a naturally occurring amino acid covalently linked to $A^2$ at its α-amino group through an amide bond.

2. The ligand-agent conjugate of claim 1 comprising a metabolically labile linker L.

3. The ligand-agent conjugate of claim 2 wherein the metabolically labile linker L is hydrolytically or reductively cleaved in the cell to release the diagnostic or therapeutic agent D.

4. A pharmaceutical composition comprising the ligand agent conjugate of claim 1 and at least one component selected from the group consisting of a pharmaceutically acceptable carrier, excipient, or diluent.

5. A method for delivering a diagnostic agent or a therapeutic agent to a target cell population comprising a folate receptor, the method comprising: providing a ligand-agent conjugate having the formula

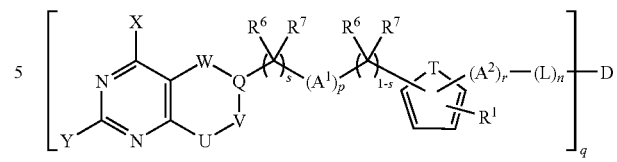

wherein X and Y are each independently selected from the group consisting of halo, $R^2$, $OR^2$, $SR^3$, and $NR^4R^5$;

U, V, and W represent divalent moieties wherein U and W are —N= or —N($R^{4"}$)— and V is —($R^{6'}$)C= or —($R^{6'}$)C($R^{7'}$)—;

Q is selected from the group consisting of C and CH;

T is selected from the group consisting of S, O, N and —C=C— such that the ring structure of which T is a member is aromatic;

$A^1$ and $A^2$ are each independently selected from the group consisting of —C(S)—, —C(Z)O—, —OC(Z)—, —N($R^{4"}$)—, —C(Z)—N($R^{4"}$)—, —N($R^{4"}$)—C(Z), —O—C(Z)—N($R^{4"}$)—, —N($R^{4"}$)—C(Z)—O—, —N($R^{4"}$)—C(Z)—N($R^{5"}$)—, —O—, —S—, —S(O)—, —S(O)$_2$—, —N($R^{4"}$)S(O)$_2$—, —C($R^{6"}$)($R^{7"}$)—, —N(C≡CH)—, —N(CH$_2$—C≡CH)—, $C_1$-$C_{12}$ alkyl and $C_1$-$C_{12}$ alkoxy; where Z is oxygen or sulfur provided that $A^2$ does not represent —C(O)NH—;

$R^1$ is selected from the group consisting of hydrogen, halo, $C_1$-$C_{12}$ alkyl, and $C_1$-$C_{12}$ alkoxy;

$R^2$, $R^3$, $R^4$, $R^{4'}$, $R^{4"}$, $R^5$, $R^{5"}$, $R^6$, and $R^7$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;

$R^6$ and $R^7$ are each independently selected from the group consisting of hydrogen, halo, $C_1$-$C_{12}$ alkyl, and $C_1$-$C_{12}$ alkoxy; or $R^6$ and $R^7$ are taken together to form O=;

$R^{6'}$ and $R^{7'}$ are each independently selected from the group consisting of hydrogen, halo, $C_1$-$C_{12}$ alkyl, and $C_1$-$C_{12}$ alkoxy; or $R^6$ and $R^7$ are taken together to form O=;

L is a divalent linker;

n, p, r and s are each independently either 0 or 1 provided when n=1, then r=1; and;

provided that the linker L does not include a naturally occurring amino acid covalently linked to $A^2$ at its α-amino group through an amide bond;

q is an integer ≧1; and

D is diagnostic agent or a therapeutic agent; and contacting the target cell population with an effective amount of ligand-agent conjugate to permit binding of the ligand-conjugate to the folate receptor.

6. The method of claim 5 wherein D is a diagnostic agent comprising a contrast agent for use in medical imaging.

7. The method of claim 5 wherein the ligand-agent conjugate binds to the cell surface and is not internalized by the cells of the cell population.

8. The method of claim 5 wherein the diagnostic or therapeutic agent D is internalized by the cells of the cell population.

9. A ligand-agent conjugate having the formula

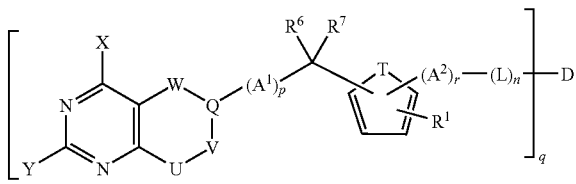

wherein
X and Y are each independently selected from the group consisting of halo, $R^2$, $OR^2$, $SR^3$, and $NR^4R^5$;
U, V, and W represent divalent moieties wherein U and W are $-N=$ or $-N(R^{4''})-$ and V is $-(R^{6'})C=$ or $-(R^{6'})C-(R^{7'})-$;
Q is selected from the group consisting of C and CH;
T is selected from the group consisting of S, O, N and $-C=C-$ such that the ring structure of which T is a member is aromatic;
$A^1$ and $A^2$ are each independently selected from the group consisting of $-C(Z)-$, $-C(Z)O-$, $-OC(Z)-$, $-N(R^{4''})-$, $-C(Z)-N(R^{4''})-$, $-N(R^{4''})-C(Z)$, $-O-C(Z)-N(R^{4''})$, $-N(R^{4''})-C(Z)-O-$, $-N(R^{4''})-C(Z)-N(R^{5''})-$, $-O-$, $-S-$, $-S(O)-$, $-S(O)_2-$, $-N(R^{4''})S(O)_2-$, $-C(R^{6''})(R^{7''})-$, $-N(C\equiv CH)-$, $-N(CH_2-C\equiv CH)-$, $C_1$-$C_{12}$ alkyl and $C_1$-$C_{12}$ alkoxy; where Z is oxygen or sulfur provided that $A^2$ does not represent $-C(O)NH-$;
$R^1$ is selected from the group consisting of hydrogen, halo, $C_1$-$C_{12}$ alkyl, and $C_1$-$C_{12}$ alkoxy;
$R^2$, $R^3$, $R^4$, $R^{4'}$, $R^{4''}$, $R^5$, $R^{5''}$, $R^6$ and $R^7$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;
$R^6$ and $R^7$ are each independently selected from the group consisting of hydrogen, halo, $C_1$-$C_{12}$ alkyl, and $C_1$-$C_{12}$ alkoxy; or $R^6$ and $R^7$ are taken together to form $O=$;
$R^{6'}$ and $R^{7'}$ are each independently selected from the group consisting of hydrogen, halo, $C_1$-$C_{12}$ alkyl, and $C_1$-$C_{12}$ alkoxy; or $R^6$ and $R^7$ are taken together to form $O=$;
L is a divalent linker;
n, p and r are each independently either 0 or 1 provided when n=1, then r=1; and;
q is an integer $\geq 1$; and
D is diagnostic agent or a therapeutic agent
provided that the linker L does not include a naturally occurring amino acid covalently linked to $A^2$ at its α-amino group through an amide bond.

10. The ligand-agent conjugate of claim 9 comprising a metabolically labile linker L.

11. The ligand-agent conjugate of claim 10 wherein the metabolically labile linker L is hydrolytically or reductively cleaved in the cell to release the diagnostic or therapeutic agent D.

12. The ligand-agent conjugate of claim 10 wherein the metabolically labile linker L comprises a disulfide or an ester.

13. A pharmaceutical composition comprising the ligand-agent conjugate of claim 9 and at least one component selected from the group consisting of a pharmaceutically acceptable carrier, excipient, or diluent.

14. A ligand-agent conjugate having the formula

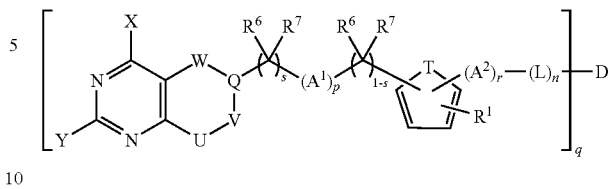

wherein
X and Y are each independently selected from the group consisting of halo, $R^2$, $OR^2$, $SR^3$, and $NR^4R^5$;
U, V, and W represent divalent moieties wherein U and W are $-N=$ or $-N(R^{4''})-$ and V is $-(R^{6'})C=$ or $-(R^{6'})C-(R^{7'})-$;
Q is selected from the group consisting of C and CH;
T is selected from the group consisting of S, O, N and $-C=C-$ such that the ring structure of which T is a member is aromatic;
$A^1$ and $A^2$ are each independently selected from the group consisting of $-C(Z)-$, $-C(Z)O-$, $-OC(Z)-$, $-N(R^{4''})-$, $-C(Z)-N(R^{4''})-$, $-N(R^{4''})-C(Z)$, $-O-C(Z)-N(R^{4''})-$, $-N(R^{4''})-C(Z)-O-$, $-N(R^{4''})-C(Z)-N(R^{5''})-$, $-O-$, $-S-$, $-S(O)-$, $-S(O)_2-$, $-N(R^{4''})S(O)_2-$, $-C(R^{6''})(R^{7''})-$, $-N(C\equiv CH)-$, $-N(CH_2-C\equiv CH)-$, $C_1$-$C_{12}$ alkyl and $C_1$-$C_{12}$ alkoxy; where Z is oxygen or sulfur provided that $A^2$ does not represent $-C(O)NH-$;
$R^1$ is selected from the group consisting of hydrogen, halo, $C_1$-$C_{12}$ alkyl, and $C_1$-$C_{12}$ alkoxy;
$R^2$, $R^3$, $R^4$, $R^{4'}$, $R^{4''}$, $R^5$, $R^{5''}$, $R^6$ and $R^7$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;
$R^6$ and $R^7$ are each independently selected from the group consisting of hydrogen, halo, $C_1$-$C_{12}$ alkyl, and $C_1$-$C_{12}$ alkoxy; or $R^6$ and $R^7$ are taken together to form $O=$;
$R^{6'}$ and $R^{7'}$ are each independently selected from the group consisting of hydrogen, halo, $C_1$-$C_{12}$ alkyl, and $C_1$-$C_{12}$ alkoxy; or $R^6$ and $R^7$ are taken together to form $O=$;
L is a metabolically labile divalent linker comprising a disulfide or an ester;
n, p, r and s are each independently either 0 or 1 provided when n=1, then r=1;
q is an integer $\geq 1$;
D is diagnostic agent or a therapeutic agent; and
provided that the linker L does not include a naturally occurring amino acid covalently linked to $A^2$ at its α-amino group through an amide bond.

15. The ligand-agent of claim 14 wherein the metabolically labile linker L is hydrolytically or reductively cleaved in the cell to release the diagnostic or therapeutic agent D.

16. A ligand-agent conjugate having the formula

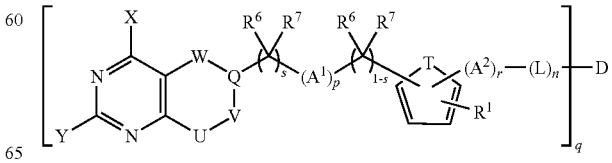

wherein
- X and Y are each independently selected from the group consisting of halo, $R^2$, $OR^2$, $SR^3$, and $NR^4R^5$;
- U, V, and W represent divalent moieties wherein U and W are —N= or —N($R^{4''}$)— and V is —($R^{6'}$)C= or —($R^{6'}$)C($R^{7'}$)—;
- Q is selected from the group consisting of C and CH;
- T is selected from the group consisting of S, O, and N such that the ring structure of which T is a member is aromatic;
- $A^1$ and $A^2$ are each independently selected from the group consisting of —C(Z)—, —C(Z)O—, —OC(Z)—, —N($R^{4''}$)—, —C(Z)—N($R^{4''}$)—, —N($R^{4''}$)—C(Z), —O—C(Z)—N($R^{4''}$)—, —N($R^{4''}$)—C(Z)—O—, —N($R^{4''}$)—C(Z)—N($R^{5''}$)—, —O—, —S—, —S(O)—, —S(O)$_2$—, —N($R^{4''}$)S(O)$_2$—, —C($R^{6''}$)($R^{7''}$)—, —N(C≡CH)—, —N(CH$_2$—C≡CH)—, $C_1$-$C_{12}$ alkyl and $C_1$-$C_{12}$ alkoxy; where Z is oxygen or sulfur provided that $A^2$ does not represent —C(O)NH—;
- $R^1$ is selected from the group consisting of hydrogen, halo, $C_1$-$C_{12}$ alkyl, and $C_1$-$C_{12}$ alkoxy;
- $R^2$, $R^3$, $R^4$, $R^{4'}$, $R^{4''}$, $R^5$, $R^{5''}$, $R^6$ and $R^7$ are each independently selected from the group consisting of hydrogen, halo, $C_1$-$C_{12}$ alkyl, $C_1$-$C_{12}$ alkoxy, $C_1$-$C_{12}$ alkanoyl, $C_1$-$C_{12}$ alkenyl, $C_1$-$C_{12}$ alkynyl, ($C_1$-$C_{12}$ alkoxy)carbonyl, and ($C_1$-$C_{12}$ alkylamino)carbonyl;
- $R^6$ and $R^7$ are each independently selected from the group consisting of hydrogen, halo, $C_1$-$C_{12}$ alkyl, and $C_1$-$C_{12}$ alkoxy; or $R^6$ and $R^7$ are taken together to form O=;
- $R^{6'}$ and $R^{7'}$ are each independently selected from the group consisting of hydrogen, halo, $C_1$-$C_{12}$ alkyl, and $C_1$-$C_{12}$ alkoxy; or $R^6$ and $R^7$ are taken together to form O=;
- L is a divalent linker;
- n, p, r and s are each independently either 0 or 1 provided when n=1, then r=1;
- q is an integer ≧1;
- D is diagnostic agent or a therapeutic agent; and
- provided that the linker L does not include a naturally occurring amino acid covalently linked to $A^2$ at its α-amino group through an amide bond.

17. A pharmaceutical composition comprising the ligand agent conjugate of claim 16 and at least one component selected from the group consisting of a pharmaceutically acceptable carrier, excipient, or diluent.

* * * * *

UNITED STATES PATENT AND TRADEMARK OFFICE
CERTIFICATE OF CORRECTION

PATENT NO. : 7,875,612 B2
APPLICATION NO. : 10/475876
DATED : January 25, 2011
INVENTOR(S) : Mark A Green, Chun-Yen Ke and Christopher P Leamon It is certified that error appears in the above-identified patent and that said Letters Patent is hereby corrected as shown below:

Claim 1, column 23, lines 15-16 replace the text "—$(R^6)$C—$(R^{7'})$—" with the text -- —$(R^{6'})$C$(R^{7'})$— --

Claim 1, column 23, line 33 replace the text "$R^2$, $R^3$, $R^4$, $R^{4'}$, $R^{4''}$, $R^5$, $R^{5''}$, $R^6$ and $R^7$" with the text -- $R^2$, $R^3$, $R^4$, $R^{4'}$, $R^{4''}$, $R^5$, $R^{5''}$, $R^{6'}$ and $R^{7'}$ --

Claim 1, column 23, line 44 replace the text "$R^6$ and $R^7$" with the text -- $R^{6'}$ and $R^{7'}$ --

Claim 5, column 24, line 34 replace the text "$R^2$, $R^3$, $R^4$, $R^{4'}$, $R^{4''}$, $R^5$, $R^{5''}$, $R^6$ and $R^7$" with the text -- $R^2$, $R^3$, $R^4$, $R^{4'}$, $R^{4''}$, $R^5$, $R^{5''}$, $R^{6'}$ and $R^{7'}$ --

Claim 5, column 24, line 45 replace the text "$R^6$ and $R^7$" with the text -- $R^{6'}$ and $R^{7'}$ --

Claim 9, column 25, lines 17-18 replace the text "—$(R^6)$C—$(R^{7'})$—" with the text -- —$(R^{6'})$C$(R^{7'})$— --

Claim 9, column 25, line 35 replace the text "$R^2$, $R^3$, $R^4$, $R^{4'}$, $R^{4''}$, $R^5$, $R^{5''}$, $R^6$ and $R^7$" with the text -- $R^2$, $R^3$, $R^4$, $R^{4'}$, $R^{4''}$, $R^5$, $R^{5''}$, $R^{6'}$ and $R^{7'}$ --

Claim 9, column 25, line 45 replace the text "$R^6$ and $R^7$" with the text -- $R^{6'}$ and $R^{7'}$ --

Claim 14, column 26, lines 15-16 replace the text "—$(R^{6'})$C—$(R^{7'})$—" with the text -- —$(R^{6'})$C$(R^{7'})$— --

Claim 14, column 26, line 33 replace the text "$R^2$, $R^3$, $R^4$, $R^{4'}$, $R^{4''}$, $R^5$, $R^{5''}$, $R^6$ and $R^7$" with the text -- $R^2$, $R^3$, $R^4$, $R^{4'}$, $R^{4''}$, $R^5$, $R^{5''}$, $R^{6'}$ and $R^{7'}$ --

Claim 14, column 26, line 43 replace the text "$R^6$ and $R^7$" with the text -- $R^{6'}$ and $R^{7'}$ --

Signed and Sealed this
Twentieth Day of December, 2011

David J. Kappos
*Director of the United States Patent and Trademark Office*

CERTIFICATE OF CORRECTION (continued)
U.S. Pat. No. 7,875,612 B2

Claim 16, column 27, line 22 replace the text "$R^2$, $R^3$, $R^4$, $R^{4'}$, $R^{4''}$, $R^5$, $R^{5''}$, $R^6$ and $R^7$" with the text -- $R^2$, $R^3$, $R^4$, $R^{4'}$, $R^{4''}$, $R^5$, $R^{5''}$, $R^{6''}$ and $R^{7''}$ --

Claim 16, column 28, line 9 replace the text "$R^6$ and $R^7$" with the text -- $R^{6'}$ and $R^{7'}$ --